US010857129B2

(12) United States Patent
Holsboer

(10) Patent No.: US 10,857,129 B2
(45) Date of Patent: Dec. 8, 2020

(54) $V_{1B}$ RECEPTOR ANTAGONIST FOR USE IN THE TREATMENT OF PATIENTS HAVING AN ELEVATED AVP LEVEL AND/OR AN ELEVATED COPEPTIN LEVEL

(71) Applicant: B.R.A.H.M.S GMBH, Hennigsdorf (DE)

(72) Inventor: Florian Holsboer, Munich (DE)

(73) Assignee: B.R.A.H.M.S GMBH, Hennigsdorf (DE)

( * ) Notice: Subject to any disclaimer, the term of this patent is extended or adjusted under 35 U.S.C. 154(b) by 0 days.

(21) Appl. No.: 16/541,622

(22) Filed: Aug. 15, 2019

(65) Prior Publication Data

US 2019/0365708 A1 Dec. 5, 2019

Related U.S. Application Data

(60) Division of application No. 15/794,520, filed on Oct. 26, 2017, now abandoned, which is a continuation of application No. 14/407,594, filed as application No. PCT/EP2013/062552 on Jun. 17, 2013, now abandoned.

(30) Foreign Application Priority Data

Jun. 15, 2012 (GB) .................................. 1210686.0

(51) Int. Cl.
*C12Q 1/68* (2018.01)
*A61K 31/405* (2006.01)
*C07K 14/72* (2006.01)
*A61K 45/06* (2006.01)
*A61K 31/404* (2006.01)
*A61K 31/573* (2006.01)
*C12Q 1/6883* (2018.01)
*G01N 33/68* (2006.01)
*G01N 33/574* (2006.01)

(52) U.S. Cl.
CPC .......... *A61K 31/405* (2013.01); *A61K 31/404* (2013.01); *A61K 31/573* (2013.01); *A61K 45/06* (2013.01); *C07K 14/723* (2013.01); *C12Q 1/6883* (2013.01); *G01N 33/57407* (2013.01); *G01N 33/57434* (2013.01); *G01N 33/68* (2013.01); *G01N 33/6893* (2013.01); *C12Q 2600/106* (2013.01); *C12Q 2600/156* (2013.01); *G01N 2800/048* (2013.01); *G01N 2800/301* (2013.01); *G01N 2800/304* (2013.01); *G01N 2800/52* (2013.01)

(58) Field of Classification Search
None
See application file for complete search history.

(56) References Cited

U.S. PATENT DOCUMENTS

| 6,060,478 | A | 5/2000 | Gilligan et al. |
| 6,107,301 | A | 8/2000 | Aldrich et al. |
| 6,586,456 | B1 | 7/2003 | Fontaine et al. |
| 7,067,664 | B1 | 6/2006 | Chen |
| 8,420,679 | B2 | 4/2013 | Fontaine et al. |
| 10,190,168 | B2 | 1/2019 | Holsboer et al. |
| 2003/0092019 | A1 | 5/2003 | Meyer et al. |
| 2005/0069936 | A1 | 3/2005 | Diamond et al. |
| 2006/0240419 | A1 | 10/2006 | Nakamura et al. |
| 2007/0281919 | A1 | 12/2007 | Fontaine et al. |
| 2008/0118918 | A1 | 5/2008 | Licinio et al. |
| 2008/0194589 | A1 | 8/2008 | Lanier et al. |
| 2008/0318923 | A1 | 12/2008 | Sekiguchi et al. |
| 2009/0221009 | A1 | 9/2009 | Bergmann et al. |
| 2009/0306137 | A1 | 12/2009 | Wolfgang et al. |
| 2010/0184742 | A1* | 7/2010 | Uhr ................ C12Q 1/6883 514/214.02 |
| 2012/0115842 | A1 | 5/2012 | Lubisch et al. |
| 2012/0208195 | A1 | 8/2012 | De Rijk et al. |
| 2015/0094310 | A1 | 4/2015 | Holsboer |
| 2015/0150846 | A1 | 6/2015 | Holsboer |
| 2015/0278438 | A1 | 10/2015 | Muller-Myhsok et al. |
| 2016/0153043 | A1 | 6/2016 | Holsboer et al. |

(Continued)

FOREIGN PATENT DOCUMENTS

| EP | 0773023 A1 | 5/1997 |
| EP | 1659121 A1 | 5/2006 |
| JP | H09-507249 A | 7/1997 |

(Continued)

OTHER PUBLICATIONS

Morgenthaler et al. (Trends in Endocrinology and Metabolism 2008 vol. 19 p. 43) (Year: 2008).*
U.S. Appl. No. 14/396,477, filed Oct. 23, 2014.
U.S. Appl. No. 14/396,617, filed Oct. 23, 2014.
U.S. Appl. No. 14/407,594, filed Dec. 12, 2014.
U.S. Appl. No. 14/898,877, filed Dec. 16, 2015.
U.S. Appl. No. 15/794,520, filed Oct. 26, 2017.
U.S. Appl. No. 16/230,123, filed Dec. 21, 2018.

(Continued)

*Primary Examiner* — Katherine D Salmon
(74) *Attorney, Agent, or Firm* — Millen White Zelano and Branigan, PC; John Sopp

(57) ABSTRACT

The present invention relates to a vasopressin receptor 1B ($V_{1B}$) antagonist for use in the treatment of depressive symptoms and/or anxiety symptoms in patients showing an elevated arginine vasopressin (AVP) level and/or an elevated copeptin level. The present invention further relates to a method for predicting the treatment response to a $V_{1B}$ antagonist in patients with depressive symptoms and/or anxiety symptoms.

7 Claims, 2 Drawing Sheets

Specification includes a Sequence Listing.

(56) References Cited

U.S. PATENT DOCUMENTS

| | | |
|---|---|---|
| 2018/0042898 A1 | 2/2018 | Holsboer |
| 2019/0194752 A1 | 6/2019 | Holsboer et al. |

FOREIGN PATENT DOCUMENTS

| | | | |
|---|---|---|---|
| JP | 2008-509674 A | 4/2008 | |
| JP | 2008-510151 A | 4/2008 | |
| JP | 2008-526702 A | 7/2008 | |
| JP | 2009-538331 A | 11/2009 | |
| WO | WO 1994/013676 A1 | 6/1994 | |
| WO | WO 1995/033750 A1 | 12/1995 | |
| WO | WO 96/09526 A1 | 3/1996 | |
| WO | WO 1997/029109 A1 | 8/1997 | |
| WO | WO 1998/003510 A1 | 1/1998 | |
| WO | WO 2001/005776 A1 | 1/2001 | |
| WO | WO 2002/072202 A1 | 9/2002 | |
| WO | WO 2003/097877 A1 | 11/2003 | |
| WO | WO 2004/047866 A2 | 6/2004 | |
| WO | WO 2009/130232 A1 | 10/2004 | |
| WO | WO 2004/094420 A1 | 11/2004 | |
| WO | WO 2006/017854 A2 | 2/2006 | |
| WO | WO 2006/044958 A1 | 4/2006 | |
| WO | WO 2006/072458 A2 | 7/2006 | |
| WO | WO 2006/080574 A1 | 8/2006 | |
| WO | WO 2007/137227 A1 | 11/2007 | |
| WO | WO 2008/080973 A1 | 7/2008 | |
| WO | WO 2009/113985 A1 | 9/2009 | |
| WO | WO 2013/160315 A2 | 10/2013 | |
| WO | WO 2013/160317 A2 | 10/2013 | |
| WO | WO 2013/186399 A1 | 12/2013 | |

OTHER PUBLICATIONS

Ben-Efraim et al., "Family-Based Study of AVPR1B Association and Interaction with Stressful Life Events on Depression and Anxiety in Suicide Attempts," *Neuropsychopharmacology*, 38(8): 1504-1511 (2013).
Binneman et al., "A 6-Week Randomized, Placebo-Controlled Trial of CP-316,311 (a Selective $CRH_1$ Antagonist) in the Treatment of Major Depression," *Am. J. Psychiatry*, 165(5): 617-620 (2008).
Brenner et al., *Nature Biotechnology*, 18: 630-634 (2000).
Broad Institute, "SNAP: SNP Annotation and Proxy Search," http://www.broadinstitute.org/mpg/snap (downloaded Apr. 22, 2015).
Brouwer et al., "Prediction of treatment response by HPA-axis and glucocorticoid receptor polymorphisms in major depression," *Psychoneuroendocrinology*, 31(10): 1154-1163 (2006).
Budziszewska et al., "Regulation of the Human Coricotropin-Releasing-Hormone Gene Promoter Activity by Antidepressant Drugs in Neuro-2A and AtT-20 Cells," *Neuropsychopharmacology*, 29(4): 785-794 (2004).
Carlson et al., "Selecting a Maximally Informative Set of Single-Nucleotide Polymorphisms for Association Analyses Using Linkage Disequilibrium," *Am. J. Hum. Genet.*, 74(1): 106-120 (2004).
Carpenter et al., "Cerebrospinal Fluid Corticotropin-Releasing Factor and Perceived Early-Life Stress in Depressed Patients and Healthy Control Subjects," *Neuropsychopharmacology*, 29(4): 777-784 (2004).
Chen et al., "Synthesis and SAR of 2-Aryloxy-4-alkoxy-pyridines as Potent Orally Active Corticotropin-Releasing Factor 1 Receptor Antagonists," *Journal of Medicinal Chemistry*, 51(5): 1377-1384 (2008).
Coplan et al., "Persistent elevations of cerebrospinal fluid concentrations of corticotropin-releasing factor in adult nonhuman primates exposed to early-life stressors: Implications for the pathophysiology of mood and anxiety disorders," *Proc. Natl. Acad. Sci. USA*, 93(3): 1619-1623 (1996).
Coric et al., "Multicenter, Randomized, Double-Blind, Active Comparator and Placebo-Controlled Trial of a Corticotropin-Releasing Factor Receptor-1 Antagonist in Generalized Anxiety Disorder," *Depress Anxiety*, 27(5): 417-425 (2010).
Crisafulli et al., "Pharmacogenetics of Antidepressants," *Frontiers in Pharmacology*, 2: Article 6 [21 pages] (Feb. 16, 2011).
Dabla et al., *Clinica Chimica Acta*, 412: 22-28 (2011).
Dempster, "Evidence of an Association Between the Vasopressin V1b Receptor Gene (AVPR1B) and Childhood-Onset Mood Disorders," *Archives of General Psychiatry*, 64(10): 1189 (2007).
Devlin et al., "A Comparison of Linkage Disequilibrium Measures for Fine-Scale Mapping," *Genomics*, 29(2): 311-322 (1995).
Evaluatepharma, "Should Neurocrine get stressed over CFR1 failure" (Sep. 16, 2010) [obtained from internet at http://www.evaluategroup.com/Universal/View.aspx?type=Story&id=224081&sectionID=&isEPVantage=yes].
Gabriel et al., "The Structure of Haplotype Blocks in the Human Genome," *Science*, 296(5576): 2225-2229 (2002).
Griebel, *PNAS* 99(9): 6370-6375 (2002).
Griebel et al., "The Vasopressin V1b Receptor Antagonist SSR149415 I nthe Treatment of Major Depressive and Generalized Anxiety Disorders: Results from 4 Radomized, Double-Blind, Placebo-Controlled Studies," *J. Clin. Psychiatry*, 73(11): 1403-1411 (2012).
Griebel et al., *Nature Reviews Drug Discovery* 2012 11(6): 462-478 (2012).
Griebel et al., *Curr. Pharm. Design*, 11: 1549-1559 (2005).
Hamilton, *J. Neurol. Neurosurg. Psychiatry*, 23: 56-62 (1960).
Heim et al., "The Dexamethasone/Corticotropin-Releasing Factor Test in Men with Major Depression: Role of Childhood Trauma," *Biol. Psychiatry*, 63(4): 398-405 (2008).
Hennings et al., *J. Psychiatr. Res.*, 43: 215-229 (2009).
Heuser et al., *J. Psychiatr. Res.*, 28(4): 341-356 (1994).
Holsboer, "CNHR1 Antagonists as Novel Treatment Strategies," *CNS Spectrum*, 6(7): 590-594 (2001).
Holsboer, "The rationale for corticotropin-releasing hormone receptor (CRH-R) antagonists to treat depression and anxiety," *J. Psychiatry Res.*, 33(3): 181-214 (1999).
Holsboer, "High-Quality Antidepressant Discovery by Understanding Stress Hormone Physiology," *Ann. N.Y. Acad. Sci.*, 1007: 394-404 (2003).
Holsboer, "How can we realize the promise of personalized antidepressant medicines?," *Nature Reviews Neuroscience*, 9: 638-646 (2008).
Ising et al., "$CRH_1$ Receptor Antagonists for the Treatment of Depression and Anxiety," *Exp. Clin. Psychoparmacol.*, 15(6): 519-528 (2007).
Ising et al., "The combined dexamethasone/CRH test as a potential surrogate marker in depression," *Progress in Neuro-Psychopharmacology & Biological Psychiatry*, 29(6): 1085-1093 (2005).
Ising, "A Genomewide Association Study Points to Multiple Loci That Predict Antidepressant Drug Treatment Outcome in Depression," *Archives of General Psychiatry*, 66(9): 966-975 (2009).
Ishizuka et al., *Neuroscience Research* 66(3): 233-237 (2010).
Juppner (Bone 1995 vol. 17, No. 2, Supplement 39S-42S).
Katan et al., *Neuroendocrinol. Lett.*, 29(3): 341-346 (2008).
Keck et al., "Combined Effects of ExonicPolymorphisms in CRHR1 and AVPR1B Genes in a Case-Control Study for Panic Disorder," *American Journal of Medical Genetics Part B (Neuropsychiatric Genetics)*, 147B: 1196-1204 (2008).
Keck et al., "Vasopressin mediates the response of the combined dexamethasone/CRH test in hyper-anxious rats: implications for pathogenesis of affective disorders," *Neuropsychopharmacology*, 26(1): 94-105 (2002).
Kimura et al., "Conditional corticotropin-releasing hormone overexpression in the mouse forebrain enhances rapid eye movement sleep," *Mol. Psychiatry*, 15(2): 154-165 (2010).
Künzel et al., "Pharmacological and Nonpharmacological Factors Influencing Hypothalamic-Pituitary-Adrenocortical Axis Reactivity in Acutely Depressed Psychiatric In-patients, Measured by the Dex-CRH Test," *Neuropsychopharmacology*, 28(12): 2169-78 (2003).
Landgraf, *CNS & Neurological Disorders—Drug Targets*, 5: 167-179 (2006).
Leszczynska-Rodziewicz et al., "Association between functional polymorphism of the AVPR1b gene and polymorphism rs1293651 of the CRHR1 gene and bipolar disorder with psychotic features," *Journal of Affective Disorders*, 138(3): 490-493 (2012).

(56) References Cited

OTHER PUBLICATIONS

Licinio et al., "Association of a corticotropin-releasing hormone receptor 1 haplotype and antidepressant treatment response in Mexican-Americans," *Molecular Psychiatry*, 9(12): 1075-1082 (2004).

Liu et al., "Association of corticotropin-releasing hormone receptor1 gene SNP and haplotype with major depression," *Neuroscience Letters*, 484(3): 358-362 (2006).

Liu et al., "Association study of corticotropin-releasing hormone receptor 1 gene polymorphisms and antidepressant response in major depressive disorders," *Neuroscience Letters*, 414(2): 155-158 (2007).

Mardis, *Annu. Rev. Genomics Hum. Genet.*, 9: 387-402 (2008).

Max Planck Institute of Psychiatry, "MARS—The Munich Antidepressant Response Signature Project," www.mars-depression.de (downloaded Apr. 22, 2015).

Morgenthaler et al., *Clin. Chem.*, 52(1): 112-119 (2006).

Moore et al., "Molecular Diagnostics for the Clinical Laboratorian," William B. Coleman and Gregory J. Tsongalis, Editors, Humana Press (2007).

Müller et al., "Limbic corticotropin-releasing hormone receptor 1 mediates anxiety-related behavior and hormonal adaptation to stress," *Nat. Neurosci.*, 6(10): 1100-1107 (2003).

Murgatroyd et al., "Dynamic DNA methylation programs persistent adverse effects of early-life stress", *Nature Neuroscience*, 12(12): 1559-1566 (2009).

Nemeroff et al., "Elevated concentrations of CSF corticotropin-releasing factor-like immunoreactivity in depressed patients," *Science*, 226(4680): 1342-1344 (1984).

Nemeroff et al., "Reduced Corticotropin Releasing Factor Binding Sites in the Frontal Cortex of Suicide Victims," *Arch. Gen. Psychiatry*, 145(6): 577-579 (1988).

Nickel et al., *BMC Medicine* 10(1): p. 7 (2012).

Oost et al., *Biorg. Med. Chem. Lett.*, 21: 3828-3831 (2011).

Overstreet et al., "Antidepressant-like effects of the vasopressin V1b receptor antagonist SSR149415 in the Flinders Sensitive Line rat," *Pharmacology, Biochemistry and Behavior*, 82: 223-227 (2005).

Paez-Pereda et al., "Corticotropin releasing factor receptor antagonists for major depressive disorder," *Expert Opin. Investig. Drugs*, 20(4): 519-35 (2011).

Purba et al., "Increased number of vasopressin- and oxytocin-expressing neurons in the paraventricular nucleus of the hypothalamus in depression," *Arch Gen Psychiatry*, 53(2): 137-143 (1996).

Rechtschaffen & Kales (Eds.), *A Manual of Standardized Terminology Techniques and Scoring System for Sleep Stages of Human Subjects*, BIS/BRI, UCLA, Los Angeles, 1968.

Ripke et al., "A mega-analysis of genome-wide association studies for major depressive disorder," *Molecular Psychiatry*, 18(4): 497-511 (2012).

Roberts, Stuart (Analyst, Southern Cross Equities), "Bionomics (BNO): Anxiety can be a good thing," pp. 1-37 (Apr. 11, 2011) [obtained from internet at http://www.bionomics.com.au/siteFiles/files/Sourthern%20Cross%20Equities%20-%2011Apr11.pdf].

Sánchez et al., "Early adverse experience as a developmental risk factor for later psychopathology: Evidence from rodent and primate models," *Dev. Psychopathol.*, 13(3): 419-49 (2001).

Schüle et al., *PLoS ONE*, 4(1): e4324 (2009).

Schuster, *Nat. Methods*, 5(1): 16-18 (2008).

Spencer et al., "Designing Genome-Wide Association Studies: Sample Size, Power, Imputation, and the Choice of Genotyping Chip," *PLOS Genetics*, 5(5): e100047715 (2009).

Serradeil-Le Gal et al., *JPET*, 300(3): 1122-1130 (2002).

Stoyanovich, "MutaGeneSys: estimating individual disease susceptibility based on genome-wide SNP array data," *Bioinformatics*, 24(3): 440-442 (2008).

Szymczak et al., "Machine Learning in Genome-Wde Association Studies," *Genetic Epidemiology*, 33(Supplement 1): S51-S57 (2009).

Thode et al., "Hypothalamic-pituitary-adrenal axis activation in response to stress is moderated by polymorphic variants within the corticotropin-releasing hormone receptor 1," *Biological Psychiatry*, 63(7-Suppl. S): 85S (2008).

Thode et al., "Hypothalamic-pituitary-adrenal axis activation in response to stress is moderated by polymorphic variants within the corticotropin-releasing hormone receptor 1," 63rd Annual Convention of the Society-of-Biological-Psychiatry, Washington, DC, USA (2008) [poster presentation retrieved from internet at http://psychiatry.uthscsa.edu/RRTrack/images/Thode_Poster_08.pdf].

Timpl et al., "Impaired stress response and reduced anxiety in mice lacking a functional corticotropin-releasing hormone receptor 1," *Nature Genetics*, 19(2): 162-166 (1998).

Trivedi et al., "Evaluation of Outcomes With Citalopram for Depression Using Measurement-Based Care in STAR*D: Implications for Clinical Practice," *Am. J. Psychiatry*, 163(1): 28-40 (2006).

Tyrka et al., "Interaction of Childhood Maltreatment with the Corticotropin-Releasing Hormone Receptor Gene: Effects on Hypothalamic-Pituitary-Adrenal Axis Reactivity," *Biological Psychiatry*, 66(7): 681-685 (2009).

Uhr et al., "Polymorphisms in the Drug Transporter Gene ABCB1 Predict Antidepressant Treatment Response in Depression," *Neuron*, 57(2): 203-209 (2008).

Van Londen et al., "Plasma levels of arginine vasopressin elevated in patients with major depression," *Neuropsychopharmacology*, 17(4): 284-292 (1997).

Van Rossum et al., "Polymorphisms of the Glucocorticoid Receptor Gene and Major Depression," *Biological Psychiatry*, 59(8): 681-688 (2006).

Van West et al., *Psychiatry Research* 179(1): 64-68 (2010).

Van West et al., "Arginine vasopressin receptor gene-based single-nucleotide polymorphism analysis in attention deficit hyperactivity disorder," *Psychiatric Genetics*, 19: 102-103 (2009).

Van West et al., "A major SNP haplotype of the arginine vasopressin IB receptor protects against recurrent major depression," *Molecular Psychiatry*, 9(3): 287-292 (2004).

Van West et al., "P.7.b.005 Arginine vasopressin receptor gene-based single nucleotide polymorphism (SNP) analysis in ADHD," *European Neuropsychopharmacology*, Elsevier Science Publishers BV, Amsterdam, NL, 19: S686 (2009).

Zobel et al., "Effects of the high-affinity corticotrophin-releasing hormone receptor 1 antagonist R121919 in major depression: the first 10 patients treated," *J. Psych. Res.*, 34: 171-181 (2000).

Zorilla et al., "Progress in corticotropin-releasing factor-1 antagonist development," *Drug Discovery Today*, 15(9/10): 371-383 (2010).

European Patent Office, International Search Report in International Patent Application No. PCT/EP2013/058411 (dated Nov. 21, 2013).

European Patent Office, Written Opinion in International Patent Application No. PCT/EP2013/058411 (dated Nov. 21, 2013).

European Patent Office, International Search Report in International Patent Application No. PCT/EP2013/058413 (dated Nov. 18, 2013).

European Patent Office, Written Opinion in International Patent Application No. PCT/EP2013/058413 (dated Nov. 18, 2013).

European Patent Office, International Search Report in International Patent Application No. PCT/EP2014/062592 (dated Oct. 14, 2014).

European Patent Office, Written Opinion in International Patent Application No. PCT/EP2014/062592 (dated Oct. 14, 2014).

European Patent Office, International Search Report in International Application No. PCT/EP2013/062552 (dated Sep. 13, 2013).

European Patent Office, Written Opinion in International Application No. PCT/EP2013/062552 (dated Sep. 13, 2013).

European Patent Office, Communication Pursuant to Article 94(3) EPC in European Patent Application No. 13717792.9 (dated May 12, 2016).

Japanese Patent Office, Notification of Reasons for Rejection in Japanese Patent Application No. 2015-516647 (dated Mar. 28, 2017).

Japanese Patent Office, Notification of Reasons for Rejection in Japanese Patent Application No. 2016/520422 (dated Dec. 25, 2018).

United Kingdom Intellectual Property Office, Combined Search and Examination Report in Great Britain Patent Application No. 1207102.3 (dated Aug. 21, 2012).

(56) References Cited

OTHER PUBLICATIONS

United Kingdom Intellectual Property Office, Combined Search and Examination Report in Great Britain Patent Application No. 1210686.0 (dated Oct. 16, 2012).

* cited by examiner

$V_{1B}$ RECEPTOR ANTAGONIST FOR USE IN THE TREATMENT OF PATIENTS HAVING AN ELEVATED AVP LEVEL AND/OR AN ELEVATED COPEPTIN LEVEL

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 2,938 bytes ASCII (Text) file named "744183_ST25.txt," created Aug. 14, 2019.

FIELD OF THE INVENTION

The present invention relates to a vasopressin receptor 1B ($V_{1B}$) antagonist for use in the treatment of depressive symptoms and/or anxiety symptoms in patients showing an elevated arginine vasopressin (AVP) level and/or an elevated copeptin level. The present invention further relates to methods for predicting a treatment response to a $V_{1B}$ antagonist in patients with depressive symptoms and/or anxiety symptoms.

BACKGROUND OF THE INVENTION

Hypotheses as to the development of depression and anxiety disorders inter alia point to the role of neuropeptides, which are involved in the central regulation of stress hormones. Besides corticotropin releasing hormone, vasopressin may also play an important role in this respect (Griebel and Holsboer (2012); *Neuropeptide receptor ligands as drugs for psychiatric diseases: the end of the beginning?*; Nat Rev Drug Discov 11: 462-479).

Vasopressin (also referred to as arginine vasopressin (AVP), vasopressin argipressin or antidiuretic hormone (ADH)) is a neuropeptide which is synthesized in the hypothalamus of mammals and exerts its action through different receptors, e.g. the $V_{1A}$ and $V_{1B}$ receptor subtype widely distributed in the central nervous system (CNS) (Griebel and Holsboer (2012); *Neuropeptide receptor ligands as drugs for psychiatric diseases: the end of the beginning?*; Nat Rev Drug Discov 11: 462-479).

In human studies the hypothesis that vasopressin plays an important role in depression and anxiety disorders is supported by increased AVP secretion from hypothalmatic neurons. Animal experiments also point to a central role of vasopressin in the development of depression and anxiety disorders (Landgraf (2006); *The Involvement of the Vasopressin System in Stress Related Disorders*; CNS & Neurological Disorders 5:167-179).

These findings lead to research and development programs of the pharmaceutical industry aiming at the development of vasopressin antagonists useful in the treatment of depression and/or anxiety disorders. However, so far clinical trials have been unsuccessful.

Hence, there is still a need for antidepressant and/or anxiolytic drugs effective in the treatment of depressive symptoms and/or anxiety symptoms in a number of psychiatric disorders as well as for methods for predicting treatment responses to $V_{1B}$ antagonists in patients suffering from depressive and/or anxiety symptoms.

SUMMARY OF THE INVENTION

It has now been found that despite the so far unsuccessful clinical trials, a specific group of patients showing depressive symptoms and/or anxiety symptoms, i.e. patients showing an elevated arginine vasopressin level and/or an elevated copeptin level, profits from the treatment with $V_{1B}$ antagonists.

It has also been found that the treatment response to $V_{1B}$ antagonists can be predicted by determining the copeptin concentration in a blood sample of a patient and/or by determining the AVP concentration in a sample of cerebrospinal fluid of said patient.

A further finding of the invention is that the presence of a polymorphic variant in the vasopressin receptor 1B (AVPR1B) gene in combination with one or more further marker(s) is indicative for an elevated arginine vasopressin level and/or copeptin level and thus for a treatment response to $V_{1B}$ antagonists.

In one aspect the present invention relates to a vasopressin receptor 1B ($V_{1B}$) antagonist for use in the treatment of depressive symptoms and/or anxiety symptoms in a patient showing an elevated arginine vasopressin (AVP) level and/or an elevated copeptin level. For example, the present invention relates to a $V_{1B}$ receptor antagonist for use in the treatment of depressive symptoms and/or anxiety symptoms in a patient showing an elevated AVP level. According to another exemplary embodiment, the present invention relates to a $V_{1B}$ receptor antagonist in the treatment of depressive symptoms and/or anxiety symptoms in a patient showing an elevated copeptin level. In another exemplary embodiment, the present invention relates to a $V_{1B}$ receptor antagonist for use in the treatment of depressive symptoms and/or anxiety symptoms in a patient showing an elevated AVP level and an elevated copeptin level.

In one embodiment the present invention relates to the $V_{1B}$ receptor antagonist for use as described above, wherein the elevated AVP level and/or the elevated copeptin level in said patient is determined by means of measurement of AVP and/or by means of copeptin measurement.

In a specific embodiment of the invention, the copeptin measurement is performed in a blood sample of said patient.

Thus, in one embodiment the present invention relates to a vasopressin receptor 1B ($V_{1B}$) antagonist for use in the treatment of depressive symptoms and/or anxiety symptoms in a patient showing an elevated level of copeptin in the blood.

In another embodiment of the invention, the patient has been pre-treated with dexamethasone prior to performance of the copeptin measurement and/or measurement of AVP.

A further embodiment of the invention relates to the $V_{1B}$ receptor antagonist for use as described above, wherein an elevated AVP level is indicated by a copeptin blood concentration of at least 5 pmol/L, optionally in the range from 5 to 7 pmol/L.

A specific embodiment of the invention relates to the $V_{1B}$ receptor antagonist for use as described above, wherein the AVP measurement is performed in a sample of cerebrospinal fluid of said patient.

Thus, in one embodiment the present invention relates to a vasopressin receptor 1B ($V_{1B}$) antagonist for use in the treatment of depressive symptoms and/or anxiety symptoms in a patient showing an elevated level of AVP in the cerebrospinal fluid.

In another embodiment of the invention, the patient showing an elevated AVP level has an AVP concentration of at least 4 pg/ml AVP, optionally in the range from 4 to 6 pg/ml AVP.

A further embodiment of the invention relates to a $V_{1B}$ receptor antagonist for use as described herein, wherein an elevated AVP level and/or an elevated copeptin level is detected by determining the presence or absence of at least one polymorphic variant in the AVPR1B gene in combination with the presence or absence of at least one polymorphic variant in the patient's genome excluding the AVPR1B gene.

In one embodiment, the polymorphic variant in the AVPR1B gene and/or in the patient's genome excluding the AVPR1B gene is a single nucleotide polymorphism (SNP).

In particular, the polymorphic variant in the AVPR1B gene is SNP rs28373064, which is represented by a single polymorphic change at position 27 of SEQ ID NO: 2, wherein in one or two alleles of the wild-type nucleotide A is replaced by indicator nucleotide G.

In another embodiment, the at least one polymorphic variant in the patient's genome excluding the AVPR1B gene is selected from the group of biomarkers comprising:

SNP rs9880583 which is represented by a single polymorphic change at position 27 of SEQ ID NO: 3, wherein in one or two alleles the wild-type nucleotide C is replaced by indicator nucleotide G, SNP rs13099050 which is represented by a single polymorphic change at position 27 of SEQ ID NO: 4, wherein in one or two alleles the wild-type nucleotide A is replaced by indicator nucleotide C, SNP rs7441352 which is represented by a single polymorphic change at position 27 of SEQ ID NO: 5, wherein in one or two alleles the wild-type nucleotide A is replaced by indicator nucleotide G, SNP rs730258 which is represented by a single polymorphic change at position 27 of SEQ ID NO: 6, wherein in one or two alleles the wild-type nucleotide C is replaced by indicator nucleotide T, SNP rs12654236 which is represented by a single polymorphic change at position 27 of SEQ ID NO: 7, wherein in one or two alleles the wild-type nucleotide A is replaced by indicator nucleotide G, SNP rs17091872 which is represented by a single polymorphic change at position 27 of SEQ ID NO: 8, wherein in one or two alleles the wild-type nucleotide A is replaced by indicator nucleotide G, SNP rs12254219 which is represented by a single polymorphic change at position 27 of SEQ ID NO: 9, wherein in one or two alleles the wild-type nucleotide C is replaced by indicator nucleotide T, SNP rs11575663 which is represented by a single polymorphic change at position 27 of SEQ ID NO: 10, wherein in one or two alleles the wild-type nucleotide A is replaced by indicator nucleotide G, SNP rs7080276 which is represented by a single polymorphic change at position 27 of SEQ ID NO: 11, wherein in one or two alleles the wild-type nucleotide A is replaced by indicator nucleotide G, SNP rs7416 which is represented by a single polymorphic change at position 27 of SEQ ID NO: 12, wherein in one or two alleles the wild-type nucleotide A is replaced by indicator nucleotide G, SNP rs12424513 which is represented by a single polymorphic change at position 27 of SEQ ID NO: 13, wherein in one or two alleles the wild-type nucleotide C is replaced by indicator nucleotide T, SNP rs1035050 which is represented by a single polymorphic change at position 27 of SEQ ID NO: 14, wherein in one or two alleles the wild-type nucleotide C is replaced by indicator nucleotide T, SNP rs9959162 which is represented by a single polymorphic change at position 27 of SEQ ID NO: 15, wherein in one or two alleles the wild-type nucleotide A is replaced by indicator nucleotide C, and/or SNP rs8088242 which is represented by a single polymorphic change at position 27 of SEQ ID NO: 16, wherein in one or two alleles the wild-type nucleotide A is replaced by indicator nucleotide G.

Another embodiment of the invention relates to a $V_{1B}$ receptor antagonist for use as described herein, wherein the group of biomarkers comprises at least 2, at least 5, at least 8 or at least 11 of the biomarkers defined herein as polymorphic variants in the patient's genome excluding the AVPR1B gene.

In another embodiment, the group of biomarkers consists of the biomarkers as defined herein as polymorphic variants in the patient's genome excluding the AVPR1B gene.

In a further embodiment, the combination of the presence or absence of SNP rs28373064 with at least 1, at least 2, at least 3, at least 4, at least 5, at least 6, at least 7, at least 8, at least 9, at least 10, at least 11, at least 12, at least 13 or all of the biomarkers as defined herein as polymorphic variants in the patient's genome excluding the AVPR1B gene is determined.

In yet another embodiment, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 is determined. In yet another embodiment the absence of SNP rs28373064 in combination with the absence of SNP rs13099050, SNP rs7441352 and SNP rs12424153 is determined. In yet another embodiment, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 and the absence of SNP rs28373064 in combination with the absence of SNP rs13099050, SNP rs7441352 and SNP rs12424153 is determined.

A further embodiment of the invention relates to a $V_{1B}$ receptor antagonist for use as described above, wherein the $V_{1B}$ antagonist is selected from the group consisting of SRR149415 (SSR149415), Org 52186, ABT-436 and/or ABT-558.

In another embodiment of the invention, the $V_{1B}$ receptor antagonist for use as described above is administered in combination with at least one further pharmaceutically active compound suitable for the treatment of depressive symptoms and/or anxiety symptoms.

In a specific embodiment of the invention, the at least one further pharmaceutically active compound is selected from selective serotonin reuptake inhibitors, serotonin-norepinephrine reuptake inhibitors, dopamine reuptake inhibitors, noradrenergic and specific serotonergic antidepressants, norepinephrine (noradrenaline) reuptake inhibitors, selective serotonin reuptake enhancers, norepinephrine-dopamine disinhibitors, norepinephrine-dopamine reuptake inhibitors, tricyclic antidepressants, tetracyclic antidepressants, monamine oxidase inhibitors, psychostimulants, mood stabilizers, amine precursors, serotonin antagonists and reuptake inhibitors, anticonvulsants, nicotine, phytopharmaceuticals, melatonin receptor antagonists, 5-HT antagonists, benzodiazepines, buspirone, azapirones, barbiturates, hydroxyzine, pregabalin, corticotropin-releasing hormone receptor antagonists, neurokinin receptor antagonists, oxytocin and glucocorticoid receptor antagonists.

Another embodiment of the invention relates to the $V_{1B}$ receptor antagonist for use as described above, wherein the treatment response to the $V_{1B}$ receptor antagonist is predicted by the method as described below.

Another aspect relates to a method for predicting a treatment response to a $V_{1B}$ receptor antagonist in a patient with depressive symptoms and/or anxiety symptoms comprising the following steps:
(i) determining the presence or absence of at least one polymorphic variant in the AVPR1B gene in a nucleic acid sample of said patient and
(ii) determining the presence or absence of at least one polymorphic variant in the patient's genome excluding the AVPR1B gene in a nucleic acid sample of said patient, wherein the presence or absence of at least one polymorphic variant in the AVPR1B gene in combination with the presence or absence of at least one polymorphic variant in the patient's genome excluding the AVPR1B gene is indicative for the treatment response.

In one embodiment of said method the polymorphic variant in the AVPR1B and/or in the patient's genome excluding the AVPR1B gene is a single nucleotide polymorphism (SNP). For example, the polymorphic variant in the AVPR1B gene is an SNP. In another exemplary embodiment, the polymorphic variant in the patient's genome excluding the AVPR1B gene is an SNP.

In yet another embodiment, a polymorphic variant in the AVPR1B gene is SNP rs28373064 which is represented by a single polymorphic change at position 27 of SEQ ID NO: 2, wherein in one or two alleles of the wild-type nucleotide A is replaced by indicator nucleotide G.

In a further embodiment, the at least one polymorphic variant in the patient's genome excluding the AVPR1B is selected from the group of biomarkers comprising:
  SNP rs9880583 which is represented by a single polymorphic change at position 27 of SEQ ID NO: 3, wherein in one or two alleles the wild-type nucleotide C is replaced by indicator nucleotide G,
  SNP rs13099050 which is represented by a single polymorphic change at position 27 of SEQ ID NO: 4, wherein in one or two alleles the wild-type nucleotide A is replaced by indicator nucleotide C,
  SNP rs7441352 which is represented by a single polymorphic change at position 27 of SEQ ID NO: 5, wherein in one or two alleles the wild-type nucleotide A is replaced by indicator nucleotide G,
  SNP rs730258 which is represented by a single polymorphic change at position 27 of SEQ ID NO: 6, wherein in one or two alleles the wild-type nucleotide C is replaced by indicator nucleotide T,
  SNP rs12654236 which is represented by a single polymorphic change at position 27 of SEQ ID NO: 7, wherein in one or two alleles the wild-type nucleotide A is replaced by indicator nucleotide G,
  SNP rs17091872 which is represented by a single polymorphic change at position 27 of SEQ ID NO: 8, wherein in one or two alleles the wild-type nucleotide A is replaced by indicator nucleotide G,
  SNP rs12254219 which is represented by a single polymorphic change at position 27 of SEQ ID NO: 9, wherein in one or two alleles the wild-type nucleotide C is replaced by indicator nucleotide T,
  SNP rs11575663 which is represented by a single polymorphic change at position 27 of SEQ ID NO: 10, wherein in one or two alleles the wild-type nucleotide A is replaced by indicator nucleotide G,
  SNP rs7080276 which is represented by a single polymorphic change at position 27 of SEQ ID NO: 11, wherein in one or two alleles the wild-type nucleotide A is replaced by indicator nucleotide G,
  SNP rs7416 which is represented by a single polymorphic change at position 27 of SEQ ID NO: 12, wherein in one or two alleles the wild-type nucleotide A is replaced by indicator nucleotide G,
  SNP rs12424513 which is represented by a single polymorphic change at position 27 of SEQ ID NO: 13, wherein in one or two alleles the wild-type nucleotide C is replaced by indicator nucleotide T,
  SNP rs1035050 which is represented by a single polymorphic change at position 27 of SEQ ID NO: 14, wherein in one or two alleles the wild-type nucleotide C is replaced by indicator nucleotide T,
  SNP rs9959162 which is represented by a single polymorphic change at position 27 of SEQ ID NO: 15, wherein in one or two alleles the wild-type nucleotide A is replaced by indicator nucleotide C, and/or
  SNP rs8088242 which is represented by a single polymorphic change at position 27 of SEQ ID NO: 16, wherein in one or two alleles the wild-type nucleotide A is replaced by indicator nucleotide G.

Another embodiment of the present invention relates to the method according to the invention, wherein the group of biomarkers for which the presence or absence is determined wherein the group of biomarkers comprises at least 2, at least 5, at least 8 or at least 11 of the biomarkers in the patient's genome excluding the AVPR1B gene defined herein. For example, the presence or absence of at least 2, at least 5, at least 8 or at least 11 polymorphic variants or biomarkers as defined above is determined in step (ii) of the method described above.

In a further embodiment, the group of biomarkers for which the presence or absence is determined consists of the biomarkers in the patient's genome excluding the AVPR1B gene defined herein. For example, the presence or absence of all 14 polymorphic variants or biomarkers in the patient's genome excluding the AVPR1B gene as defined above are determined in step (ii) of the method described above.

In another embodiment, the combination of the presence or absence of SNP rs28373064 with the presence or absence of at least 1, at least 2, at least 3, at least 4, at least 5, at least 6, at least 7, at least 8, at least 9, at least 10, at least 11, at least 12, at least 13 or all of the biomarkers in the patient's genome excluding the AVPR1B gene as defined herein is determined.

In yet another embodiment, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 is determined. In yet another embodiment the absence of SNP rs28373064 in combination with the absence of SNP rs13099050, SNP rs7441352 and SNP rs12424153 is determined. In one embodiment, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 and the absence of SNP rs28373064 in combination with the absence of SNP rs13099050, SNP rs7441352 and SNP rs12424153 is determined.

Another aspect of the invention relates to a method for predicting a treatment response to a $V_{1B}$ receptor antagonist in a patient with depressive symptoms and/or anxiety symptoms, wherein the copeptin concentration in a blood sample of said patient is determined and/or the AVP concentration in a sample of cerebrospinal fluid of said patient is determined and wherein an elevated copeptin and/or an elevated AVP concentration is indicative for a patient responding to a treatment with a $V_{1B}$ receptor antagonist.

In another embodiment of the invention, the above method further comprises a step of pre-treating the patient with dexamethasone and subsequently determining the copeptin concentration in the blood sample and/or the AVP concentration in the sample of cerebrospinal fluid.

In a further embodiment of the invention, the above described method further comprises subjecting the patient to at least one combined dexamethasone/corticotropin releasing hormone test (dex/CRH test).

In another embodiment of the above described method, the copeptin concentration indicative for a patient responding to a treatment with a vasopressin receptor antagonist is at least 5 pmol/L, optionally in the range of 5-7 pmol/L.

In a further embodiment of the above described method, the elevated AVP concentration indicative for a patient responding to a treatment with a $V_{1B}$ receptor antagonist is at least 4 pg/ml AVP, optionally 4 to 6 pg/ml AVP.

DETAILED DESCRIPTION OF THE INVENTION

Figure 1:
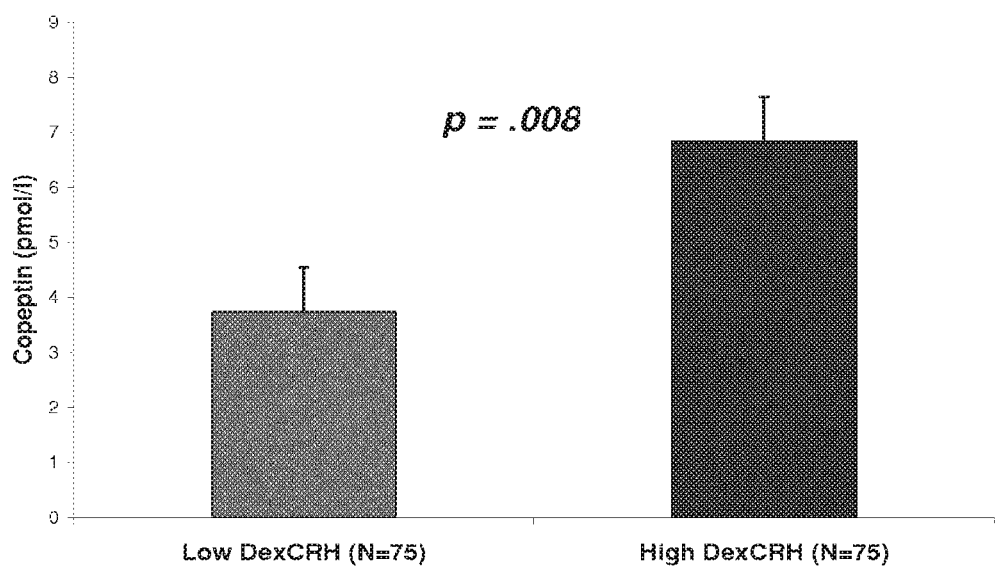
FIG. 1: Plasma copeptin levels at the first dex/CRH test in 75 patients with low and 75 patients with high HPA axis dysregulations according to this test.

Where the term "comprise" or "comprising" is used in the present description and claims, it does not exclude other elements or steps. For the purpose of the present invention, the term "consisting of" is considered to be an optional embodiment of the term "comprising of". If hereinafter a group is defined to comprise at least a certain number of embodiments, this is also to be understood to disclose a group which optionally consists only of these embodiments.

Where an indefinite or a definite article is used when referring to a singular noun such as "a" or "an" or "the", this includes a plural form of that noun unless specifically stated. Vice versa, when the plural form of a noun is used it refers also to the singular form. For example, when $V_{1B}$ antagonists are mentioned, this is also to be understood as a single $V_{1B}$ antagonist.

Furthermore, the terms first, second, third, (a), (b), (c) or (i), (ii), (iii) and the like in the description and in the claims are used for distinguishing between similar elements and not necessarily for describing a sequential or chronological order. Also, if method steps are described herein in a certain order, it is to be understood that said steps do not necessarily have to be performed in the described sequential or chronological order. It is to be understood that the terms so used or the method steps described are interchangeable under appropriate circumstances and that the embodiments of the invention described herein are capable of operation in other sequences than described or illustrated herein.

As used herein "modulation of the receptor mediated activity" includes blocking of the receptor mediated activity as well as increasing the receptor mediated activity.

Further definitions of the terms will be given below in the context of which the terms are used.

While so far clinical trials have failed to demonstrate the superiority of $V_{1B}$ antagonists in the treatment of depression and/or anxiety symptoms, it has now been found that a certain patient group showing depressive symptoms and/or anxiety symptoms, i.e. patients showing an elevated arginine vasopressin level and/or an elevated copeptin level, is responsive to the treatment with $V_{1B}$ antagonists.

Hence, in one aspect the present invention relates to a $V_{1B}$ antagonist for use in the treatment of depressive symptoms and/or anxiety symptoms in a patient showing an elevated arginine vasopressin (AVP) level, e.g. an elevated AVP level in the cerebrospinal fluid.

In another aspect the present invention relates to a $V_{1B}$ antagonist for use in the treatment of depressive symptoms and/or anxiety symptoms in a patient showing an elevated copeptin level, e.g. an elevated copeptin level in the blood.

A further aspect of the present invention relates to a $V_{1B}$ antagonist for use in the treatment of depressive symptoms and/or anxiety symptoms in a patient showing both, an elevated arginine vasopressin level and an elevated copeptin level.

The patient showing an elevated AVP and/or an elevated copeptin level may be a patient showing depressive symptoms. Alternatively, the patient showing an elevated AVP and/or an elevated copeptin level may be a patient showing anxiety symptoms. Alternatively, the patient showing an elevated AVP and/or an elevated copeptin level may be a patient showing both, depressive and anxiety symptoms.

Depressive symptoms comprise inter alia low mood, low self-esteem, loss of interest or pleasure, psychosis, poor concentration and memory, social isolation, psychomotor agitation/retardation, thoughts of death or suicide, significant weight change (loss/gain), fatigue, and a feeling of worthlessness. The depressive disorders can last for weeks to lifelong disorder with periodic reoccurring depressive episodes. For the assessment of depression severity (e.g. moderate or severe depression) the Hamilton Depression Rating Scale (HAM-D) (Hamilton, J Neurol Neurosurg Psychiatry, 1960) may be used. The depression mode may be also rated by alternative scales as the Beck Depression Inventory (BDI), the Montgomery-Åsberg Depression Scale (MADRS), the Geriatric Depression Scale (GDS), the Zung Self-Rating Depression Scale (ZSRDS). It is understood within the meaning of the invention that the $V_{1B}$ antagonist for use as described herein can be used in the treatment of any of the above mentioned depressive symptoms or a combination of any of the above mentioned depressive symptoms in a patient showing an elevated arginine vasopressin level and/or an elevated copeptin level.

Anxiety symptoms comprise inter alia panic disorders, generalized anxiety disorder, phobias and posttraumatic stress disorder. Typical symptoms of anxiety are avoidance behavior which may lead to social isolation, physical ailments like tachycardia, dizziness and sweating, mental apprehension, stress and tensions. The strength of these symptoms ranges from nervousness and discomfort to panic and terror in humans or animals. Most anxiety disorders may last for weeks or even months, some of them even for years and worsen if not suitably treated. For measuring the severity of anxiety symptoms, the Hamilton Anxiety Rating Scale (HAM-A) or the State-Trait Anxiety Rating Scale (STAI) can be used. It is understood within the meaning of the invention that the $V_{1B}$ receptor antagonist for use as described herein can be used in the treatment of any of the above mentioned anxiety symptoms or a combination of any of the above mentioned anxiety symptoms in a patient showing an elevated arginine vasopressine level and/or an elevated copeptin level.

Also, the $V_{1B}$ receptor antagonists can be used for the treatment of a patient suffering from any of the depressive symptoms described herein and any of the anxiety symptoms as described herein showing an elevated arginine vasopressine level and/or an elevated copeptin level.

"Healthy individual" as used herein, denotes any person not suffering from anxiety and/or depressive symptoms. In particular, a healthy individual denotes any person having a score of 0-7 according to the Hamilton Depression Rating Scale and/or a score of 0-6 on the Montgomery-Åsberg Depression Scale and/or a score of 20-44 on the Zung Self-Rating Depression Scale and/or a score of less than 14 on the Hamilton Anxiety Rating Scale. In addition, or alternatively, a healthy individual denotes any person having a score considered to be normal in any of the known scales for assessment of depression and/or anxiety.

The neuropeptid arginine vasopressin (also denoted as vasopressin, vasopressin argipressin or antidiuretic hormone (ADH)) is a nonapeptide which is produced in the paraventricular nucleus of the hypothalamus and the supraoptic nucleus. Vasopressin has the following sequence, whereby Cys and Cys are connected via an intramolecular disulfide bond:

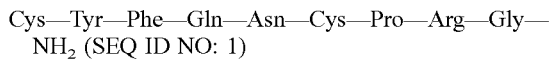
$NH_2$ (SEQ ID NO: 1)

Patients showing elevated arginine vasopressin levels as used herein include patients showing an increased gene activity of genes coding for AVP. In addition or alternatively, patients showing elevated AVP levels as used herein may include patients showing a combination of the presence or absence of at least one polymorphic variant of genes coding for the arginine vasopressine receptor (AVPR), in particular for the arginine vasopressine receptor 1B (AVPR1B), with the presence or absence of at least one polymorphic variant in the patient's genome excluding the AVPR1B gene as defined herein. Patients showing elevated arginine vasopressin levels also include patients showing elevated levels of AVP in the cerebrospinal fluid and/or patients showing elevated blood levels of AVP. Specifically, the patients showing an elevated AVP level show an elevated central AVP level, i.e. elevated AVP concentrations in the CNS.

In one embodiment the present invention relates to a $V_{1B}$ receptor antagonist for use as described herein, wherein an elevated AVP level in said patient is determined by means of AVP measurement. The measurement of AVP may be performed in a sample of cerebrospinal fluid of said patient. Samples of cerebrospinal fluid can be obtained from the patient by any method known in the art, e.g. by lumbar puncture.

Methods for determination of AVP levels in a sample of cerebrospinal fluid of a patient are known in the art and include immunoassays, e.g. radioimmunoassays. Hence, in one embodiment of the invention the AVP level in the sample of cerebrospinal fluid of the patient is measured by means of immunoassay, optionally by means of radioimmunoassay.

As used herein, an elevated AVP level denotes any AVP level higher than the AVP level measured in blood samples and/or samples of the cerebrospinal liquid of healthy individuals. Specifically, an elevated AVP level in a patient showing depressive symptoms and/or anxiety symptoms is indicated by an AVP concentration in the sample of cerebrospinal fluid of at least 4 pg/ml AVP, at least 5 pg/ml AVP, at least 6 pg/ml AVP, at least 7 pg/ml AVP, at least 8 pg/ml AVP, at least 10 pg/ml AVP, at least 20 pg/ml AVP, at least 30 pg/ml AVP, at least 50 pg/ml AVP, at least 70 pg/ml AVP or at least 90 pg/ml AVP. Elevated AVP levels may be indicated by an AVP concentration in the sample of cerebrospinal fluid in the range from 4 to 8 pg/ml AVP, optionally in the range from 4 to 6 pg/ml AVP.

Copeptin (also denoted as C-terminal proAVP) is a glycopeptide of a length of 39 amino acids which is produced from the C-terminal part of the AVP precursor. AVP and copeptin are released from the AVP precursor in an equimolar amount. Since copeptin is stable in blood (i.e. blood plasma, blood serum and/or whole blood) it provides the advantage that it may be used as surrogate marker for AVP levels in the blood plasma, blood serum and/or whole blood.

In a further embodiment the present invention thus relates to a $V_{1B}$ receptor antagonist for use as described herein, wherein an elevated AVP level and/or an elevated copeptin level in said patient is determined by means of copeptin measurement.

Methods for determination of copeptin levels in a blood sample derived from a patient are known in the art and include immunoassays, e.g. sandwich immunoassays. Examples of such immunoassays are the Copeptin EIA Kit provided by BioSupply UK, the Thermo Scientific B R A H M S copeptin Kryptor assay and the Thermo Scientific B R A H M S copeptin Kryptor us assay provided by Thermo-Scientific.

Hence, in another embodiment of the invention, the AVP level and/or copeptin level of the patient showing depressive symptoms and/or anxiety symptoms is determined by means of an immunoassay, optionally by means of a sandwich immunoassay. In another of its embodiments, the copeptin level is determined in a blood sample of the patient as defined herein. As used herein, "blood sample" relates to whole blood, blood serum and/or blood plasma. The blood sample can be obtained from the patient by any method known in the art, e.g. with a sterile needle. In a specific embodiment of the invention, the copeptin level is determined in the blood plasma derived from the blood sample of said patient. It is known in the art that blood plasma may be obtained by centrifugation of a blood sample to which an anti-coagulant has been added.

As used herein, an elevated copeptin level denotes any copeptin level higher than the copeptin level measured in blood samples of healthy individuals. Specifically, an elevated copeptin level and therefore also an elevated AVP level in a patient showing depressive symptoms and/or anxiety symptoms is indicated by a copeptin blood concentration of at least 5 pmol/L, at least 6 pmol/L, at least 7 pmol/L, at least 8 pmol/L, at least 9 pmol/L, at least 10 pmol/ml, at least 20 pmol/ml, at least 30 pmol/ml, at least 40 pmol/ml, at least 50 pmol/ml, at least 60 pmol/ml, at least 70 pmol/ml, at least 80 pmol/ml, at least 90 pmol/ml or at least 100 pmol/ml. Elevated copeptin levels and therefore also elevated AVP levels may be indicated by a copeptin blood concentration in the range from 5 to 9 pmol/L, optionally in the range from 5 to 7 pmol/L.

It is also encompassed in the invention that both the elevated copeptin level and the elevated AVP level are determined in the patient by means of copeptin measurement and measurement of AVP.

Furthermore, it has been found that the presence or absence of specific single nucleotide polymorphisms in the human genome not including the vasopressin receptor 1B (AVPR1B) gene in combination with the presence or absence of at least one specific polymorphic variant within the vasopresssin receptor 1B (AVPR1B) gene influences the response of corticotropin in an endocrine challenge test, e.g. in a combined dexamethasone (dex) supression/corticotropin releasing hormone (CRH) stimulation test. The combined dex/CRH test has been described by Heuser et al. (*The combined dexamethasone/CRH test: a refined laboratory test for psychiatric disorders.*, J Psychiatr Res, 1994, 28:341-356) and can be used for screening for compounds which may be useful in the treatment of depressive symptoms and/or anxiety symptoms. The dex/CRH test is described further below with respect to the method according to the invention. A corticotropin (ACTH) increase observed in this combined dexamethasone supression/corticotropin releasing hormone (CRH) stimulation test can be considered as a surrogate marker for an increased vasopressin level, thus indicating patients responsive to the treatment with $V_{1B}$ receptor antagonists. Since specific single nucleotide polymorphisms in the patient's genome excluding the AVPR1B gene described herein in combination with a specific polymorphic variant in the AVPR1B gene influence the response of corticotropin in the combined dex/CRH test, such polymorphic variants may be used for identifying patients showing depressive and/or anxiety symptoms having an elevated copeptin and/or vasopressin level and, consequently, showing a treatment response to $V_{1B}$ antagonists.

Thus, in another embodiment, the elevated AVP level and/or copeptin level in a patient suffering from depressive and/or anxiety symptoms can be indicated by determining the combination of the presence or absence of at least one polymorphic variant in the genes coding for the AVPR1B in a nucleic acid sample of said patient with the presence or absence of at least one polymorphic variant in the patient's genome excluding the AVPR1B gene.

A "polymorphic site" or "polymorphic variant" as used herein relates to the position of a polymorphism or SNP as described herein within the genome or portion of a genome of a subject, or within a genetic element derived from the genome or portion of a genome of a subject. In specific embodiments described herein the term "polymorphic variant" relates to a single nucleotide polymorphism (SNP).

In particular, the polymorphic variant in the AVPR1B gene and/or the patient's genome excluding the AVPR1B gene is a single nucleotide polymorphism (SNP). The term "single nucleotide polymorphism" is well understood by the skilled person and refers to a point mutation at a certain position in the nucleotide sequence. In other words, only one nucleotide differs in a certain region.

In a specific embodiment, the polymorphic variant in the AVPR1B gene is SNP rs28373064. Specifically, SNP rs28373064 is represented by a single polymorphic change at position 27 of SEQ ID NO: 2, wherein in one or two alleles of the wild-type nucleotide A is replaced by indicator nucleotide G.

Furthermore, the polymorphic variant in the patient's genome excluding the AVPR1B gene may be selected from the group of biomarkers comprising:
SNP rs9880583,
SNP rs13099050,
SNP rs7441352,
SNP rs730258,
SNP rs12654236,
SNP rs17091872,
SNP rs12254219,
SNP rs11575663,
SNP rs7080276,
SNP rs7416,
SNP rs12424513,
SNP rs1035050,
SNP rs9959162, and/or
SNP rs8088242.

The SNPs as described herein may be present on the Watson or the Crick strand, with presence of the corresponding base. If, for example, a polymorphism is present on the Watson strand as A, it is present on the Crick strand as T, if the polymorphism is present on the Watson strand as T, it is present on the Crick strand as A, if the polymorphism is present on the Watson strand as G, it is present on the Crick strand as C, and if the polymorphism is present on the Watson strand as C, it is present on the Crick strand as G, and vice versa. Also the insertion or deletion of bases may be detected on the Watson and/or the Crick strand, with correspondence as defined above. For analytic purposes the strand identity may be defined, or fixed, or may be choose at will, e.g. in dependence on factors such the availability of binding elements, GC-content etc. Furthermore, for the sake of accuracy, the SNP may be defined on both strands (Crick and Watson) at the same time, and accordingly be analyzed.

The term "allele" or "allelic sequence" as used herein refers to a particular form of a gene or a particular nucleotide, e.g. a DNA sequence at a specific chromosomal location or locus. In certain embodiments of the present invention, a SNP as defined herein may be found at or on one of two alleles in the human genome of a single subject. In further specific embodiments, a SNP as defined herein may also be found at or on both alleles in the human genome of a single subject. The presence of an indicator nucleotide or an indicator triplet as defined herein on both alleles may have a higher predictive value than the presence of an indicator nucleotide or an indicator triplet on one allele only, the other allele comprising a wild-type genotype.

The nucleotide that is present in the majority of the population is also referred to as wild-type allele or major allele. The term may further refer to the sequence of the non phenotype-associated allele with the highest prevalence within a population, e.g. within a Caucasian population. As used herein, this state is defined as "absence of a SNP".

The specific nucleotide that is present in the minority of the population is also referred as the point mutation, mutated nucleotide or minor allele. As used herein, this state is defined as "presence of a SNP", "the presence of a polymorphic variant" or "the presence of a marker".

In theory, the wild-type allele could be mutated to three different nucleotides. However, the event of a mutation to a first nucleotide in the reproductive cells of an individual that gets established in a population occurs very rarely. The event that the same position is mutated to a second nucleotide and established in the population virtually never occurs and can be therefore neglected. Therefore, as used herein, a certain nucleotide position in the genome of an individual can have two states, the wild-type state (absence of a SNP) and the mutated state (presence of a SNP).

As described above, the combination of the presence or absence of at least one polymorphic variant in the AVPR1B gene with the presence or absence of at least one polymorphic variant in the patient's genome excluding the AVPR1B gene as described herein in a sample of a patient is indicative for an elevated AVP level and/or an elevated copeptin level and, consequently, for a positive treatment response to $V_{1B}$ receptor antagonists. The at least one polymorphic variant in the patient's genome excluding the AVPR1B gene may be selected from a group of biomarkers, in particular from a group of SNPs.

The term "biomarker", as used herein, relates to any nucleic acid sequence of any length, or a derivative thereof, which comprises a polymorphic variant such as the polymorphic variant in the AVPR1B gene or the polymorphic variants in the patient's genome excluding the AVPR1B gene as defined herein. In particular, the term "biomarker" may relate to SNPs.

In addition to the combination of the presence or absence of the at least one polymorphic variant in the AVPR1B gene with the presence or absence of a polymorphic variant in the patient's genome excluding the AVPR1B gene as described herein, the presence of one or more further markers for an elevated AVP and/or copeptin level, such as clinical markers may also be determined.

In the context of the present invention "a set of biomarkers" or "group of biomarkers" relates to a combination of polymorphic variants in the patient's genome, including combinations of polymorphic variants in the AVPR1B gene and/or in the patient's genome excluding the AVPR1B gene. In particular, such a set or group of biomarkes may relate to a set comprising at least 2, at least 5, at least 8 or at least 11 of the polymorphic variants in the AVPR1B gene and/or in the patient's genome excluding the AVPR1B gene described herein in Table 1. It is understood that the set or group of biomarkers may comprise any further biomarker not explicitly described herein but considered suitable by the person skilled in the art. In one embodiment of the invention a set/group of biomarkers may consist only of the polymorphic variants in the AVPR1B gene and/or the patient's genome excluding the AVPR1B gene as described herein in Table 1.

"Combinations of polymorphic variants" as used herein may refer to the presence or absence of at least one polymorphic variant in the AVPR1B gene in combination with the presence or absence of a set or group of polymorphic variants in the patient's genome excluding the AVPR1B gene in a sample of a patient, e.g. to the presence of a combination of a polymorphic variant in the AVPR1B gene in combination with the presence of 1, 2, 3, 4, 5, 6, 7, 8, 9, 10, 11, 12, 13, or 14 polymorphic variant(s) as described herein for polymorphic variants in the patient's genome excluding the AVPR1B gene in Table 1. Combinations of polymorphic variants may relate to the presence of at least one polymorphic variant in the AVPR1B gene, optionally SNP rs28373064, in combination with the presence of 1, 2, 3, 4, 5, 6, 7, 8, 9, 10, 11, 12, 13, or 14 polymorphic variant(s) as described herein in Table 1 for polymorphic variants in the patient's genome excluding the AVPR1B gene. Combinations of polymorphic variants may also relate to the absence of at least one polymorphic variant in the AVPR1B gene, optionally SNP rs28373064, in combination with the absence of 1, 2, 3, 4, 5, 6, 7, 8, 9, 10, 11, 12, 13, or 14 polymorphic variant(s) as described herein in Table 1 for polymorphic variants in the patient's genome excluding the AVPR1B gene. Combinations of polymorphic variants may also relate to the presence of at least one polymorphic variant in the AVPR1B gene, optionally SNP rs 28373064, in combination with the absence of 1, 2, 3, 4, 5, 6, 7, 8, 9, 10, 11, 12, 13, or 14 polymorphic variant(s) as described herein in Table 1 for polymorphic variants in the patient's genome excluding the AVPR1B gene. Combinations of polymorphic variants may also relate to the absence of at least one polymorphic variant in the AVPR1B gene, optionally SNP rs28373064, in combination with the presence of 1, 2, 3, 4, 5, 6, 7, 8, 9, 10, 11, 12, 13, or 14 polymorphic variant(s) as described herein in Table 1 for polymorphic variants in the patient's genome excluding the AVPR1B gene. In one embodiment, combinations of polymorphic variants relate to the presence of at least one polymorphic variant in the AVPR1B gene, optionally SNP rs28373064, in combination with the presence of 1, 2, 3, 4, 5, 6, 7, 8, 9, 10, 11, 12, 13, or 14 polymorphic variant(s) as described herein in Table 1 for polymorphic variants in the patient's genome excluding the AVPR1B gene. In another embodiment, combinations of polymorphic variants relates to the absence of at least one polymorphic variant in the AVPR1B gene, optionally SNP rs28373064, in combination with the absence of 1, 2, 3, 4, 5, 6, 7, 8, 9, 10, 11, 12, 13, or 14 polymorphic variant(s) as described herein in Table 1 for polymorphic variants in the patient's genome excluding the AVPR1B gene.

The presence of a combination of polymorphic variants may be associated with a specific weighting factor describing the impact of the presence of such a combination on the prediction of the treatment response to a $V_{1B}$ receptor antagonist. Thus, a specific weighting factor describing the impact of the presence or absence of such a combination on the prediction of the treatment response to a $V_{1B}$ receptor antagonist may be associated with the fact that at least one polymorphic variant in the AVPR1B gene, optionally SNP rs28373064, is present and 1, 2, 3, 4, 5, 6, 7, 8, 9, 10, 11, 12, 13, or 14 polymorphic variant(s) as described herein in Table 1 (excluding SNP rs28373064) for polymorphic variants in the patient's genome excluding the AVPR1B gene is/are present, at least one polymorphic variant in the AVPR1B gene, optionally SNP rs28373064, is absent and 1, 2, 3, 4, 5, 6, 7, 8, 9, 10, 11, 12, 13, or 14 polymorphic variant(s) as described herein in Table 1 (excluding SNP rs28373064) for polymorphic variants in the patient's genome excluding the AVPR1B gene is/are absent, at least one polymorphic variant in the AVPR1B gene, optionally SNP rs28373064, is present and 1, 2, 3, 4, 5, 6, 7, 8, 9, 10, 11, 12, 13, or 14 polymorphic variant(s) as described herein in Table 1 (excluding SNP rs28373064) for polymorphic variants in the patient's genome excluding the AVPR1B gene is/are absent, at least one polymorphic variant in the AVPR1B gene, optionally SNP rs28373064, is absent and 1, 2, 3, 4, 5, 6, 7, 8, 9, 10, 11, 12, 13, or 14 polymorphic variant(s) as described herein in Table 1 (excluding SNP rs28373064) for polymorphic variants in the patient's genome excluding the AVPR1B gene is/are present.

Table 1 provides an overview over SNPs (inside and outside of the AVPR1B gene) which are, alone or in combination, indicative for an elevated AVP and/or copeptin level and thus for selecting patients suffering from depressive and/or anxiety symptoms which should respond to a treatment with a $V_{1B}$ antagonist. Hence, in one embodiment, the set or group of biomarkers consists of the biomarkers described in Table 1, whereby the presence or absence of the indicated polymorphic changes (i.e. the presence of the indicator nucleotides) as described herein is indicative for an elevated AVP and/or an elevated copeptin level. The term "indicator nucleotide" refers to a non-wild-type nucleotide at positions of SEQ ID NO: 2 to 16 as described in Table 1.

TABLE 1

| SNP_ID | Sequence | SEQ ID NO | Position of polymorphic change |
|---|---|---|---|
| rs28373064 | TCCTGCACCGGCTAGCCGGCTGGCAG[A/G]GGG CGCGCCAACAGCCGCCAGCCGA | 2 | 27 |
| rs9880583 | AAATGAAGCCACTTGTTTCTTCTCCA[C/G]CTA TGACCTAGACACCCCCTCCCCA | 3 | 27 |
| rs13099050 | AATGAATAAGAAGCCTCTCAAGACAG[A/C]AGG ATTCAACCTTATAGCTTTGATA | 4 | 27 |
| rs7441352 | TCCTCTCCCCCTATCTCTGCTTTTCA[A/G]CAT TGTACTGGAAGTCCTAGCTAAT | 5 | 27 |
| rs730258 | AGAAATAAAATCATTTCATATTCATG[C/T]AAT AGATACAAGAAATGTATTAAAG | 6 | 27 |
| rs12654236 | GGACTGTTTTTGTATTCAGTGCACAG[A/G]TGT GTGTGAAGACACCCAGCATGTT | 7 | 27 |
| rs17091872 | AATGCAAATTTTTATCAAGTACCTAC[A/G]ATG TGCGGGCAATTTTGCAAGGTGC | 8 | 27 |
| rs12254219 | CTGTGTCCTTGAAGCCCATGACAGTG[C/T]CTG ACACAAAGTAGTTGCTCAATAA | 9 | 27 |
| rs11575663 | CTTTATTTACAAAAACAAAACTGCTA[A/G]GCT TGGCCCAAGGGCCCTTATTTGC | 10 | 27 |
| rs7080276 | GTCCACGTGACTTCACACATCAGCCA[A/G]TGA GGTCTGGCCTCTGTCACCAAAC | 11 | 27 |
| rs7416 | GTAACCGGATGCATTTTTTNNNNNA[A/G]AAT TTCTCCCTTATCTACTATGATG | 12 | 27 |
| rs12424513 | GCAGCCGGACCCTGTATTGAGGAGGA[C/T]GGG CAGGGAAAGCATGCTTTAGAGA | 13 | 27 |
| rs1035050 | CTCCCCATCTTTGTATTGATGTAAGC[C/T]TCA CCTCTCTGCCCACTGGCATCCG | 14 | 27 |
| rs9959162 | TCCTCCTGATTGCCTTCAAATTAGGA[A/C]ATC AGTTGAAGTTCCTGCTTTCAGA | 15 | 27 |
| rs8088242 | AACATCTGACAAAAGGTAAGAACTCA[A/G]TAA ATGCTTTGATAGAACTTAAATA | 16 | 27 |

SNPs (together with flanking sequences) which may be used to predict the response to $V_{1B}$ receptor antagonists in patients with depressive symptoms and/or anxiety symptoms.
The position of the SNP is indicated as [wild-type nucleotide/indicator nucleotide].

One embodiment of the invention relates to a $V_{1B}$ receptor antagonist for use in the treatment of depressive symptoms and/or anxiety symptoms in a patient showing an elevated AVP and/or elevated copeptin level, wherein the elevated AVP and/or elevated copeptin level is detected or can be indicated by determining combinations of the presence or absence of at least one polymorphic variant in the AVPR1B gene with at least one polymorphic variant in the patient's genome excluding the AVPR1B gene as described in Table 1.

In yet another embodiment, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 is indicative for a treatment response to a $V_{1B}$ receptor antagonist. In yet another embodiment the absence of SNP rs28373064 in combination with the absence of SNP rs13099050, SNP rs7441352 and SNP rs12424153 is indicative for a treatment response to a $V_{1B}$ receptor antagonist. In one embodiment, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 and the absence of SNP rs28373064 in combination with the absence of SNP rs13099050, SNP rs7441352 and SNP rs12424153 is indicative for a treatment response to a $V_{1B}$ receptor antagonist. It is however to be understood that the analysis of other factors, such as the gender of the patient and the presence or absence of each of the SNPs defined in Table 1 may further add to the prediction analysis for the treatment response to a $V_{1B}$ receptor antagonist.

A person skilled in the art can derive the exact position, nucleotide sequence, and indicator sequence from the above identified rs-nomenclature, e.g. from suitable database entries and associated information systems, e.g. the Single Nucleotide Polymorphism database (dbSNP) which is incorporated herein by reference. The information may also be retrievable in case of changes to the nomenclature, or to the surrounding sequence elements, e.g. based on history functions of a suitable database.

The term "determining the presence or absence of a biomarker" or "determining the presence or absence of a polymorphic variant" as used herein refers to any suitable method or technique of detecting the identity of an SNP, e.g. at the positions of the biomarkers described herein. The determination method may be a sequencing technique or a technique based on complementary nucleic acid binding. The context of the indicated positions, as well as the strand may differ, e.g. from patient to patient, or from sample to sample etc.

Vasopressin receptor 1B ($V_{1B}$) antagonist as used herein refers to any compound capable of binding directly or indirectly to a $V_{1B}$ receptor so as to modulate the receptor mediated activity. Vasopressin receptor 1B ($V_{1B}$) antagonists as used herein include $V_{1B}$ receptor antagonists which were tested in clinical trials as well as $V_{1B}$ receptor antagonists which are currently tested in clinical trials or already admitted to the market. Various $V_{1B}$ receptor antagonists have been described in the literature and tested in clinical trials. Exemplary $V_{1B}$ receptor antagonists that have been tested in clinical trials comprise SSR149415 (also denoted as Nelivaptan; Sanofi-Aventis), Org 52186 (Organon), ABT-436 (Abbott) and ABT-558 (Abbott).

One embodiment of the present invention relates to a $V_{1B}$ receptor antagonist for use in the treatment of depressive symptoms and/or anxiety symptoms in a patient showing an elevated AVP level and/or copeptin level, wherein the $V_{1B}$ receptor antagonist is selected from the group consisting of SSR149415, Org 52186, ABT-436 and/or ABT 558. In some embodiments, a combination of any of the aforementioned $V_{1B}$ receptor antagonists may be used for treatment of depressive and/or anxiety symptoms in a patient showing an elevated AVP level and/or copeptin levels. In other embodiments, a compound selected from the group consisting of SSR149415, Org 52186, ABT-436 and/or ABT 558 may be used in combination with a further $V_{1B}$ receptor antagonist as defined herein for the treatment of depressive symptoms and/or anxiety symptoms in a patient showing an elevated AVP level and/or an elevated copeptin level. In a specific embodiment the present invention relates to a $V_{1B}$ receptor antagonist for use in the treatment of depressive symptoms and/or anxiety symptoms in a patient showing an elevated AVP level and/or copeptin level, wherein the $V_{1B}$ receptor antagonist is SSR149415. The $V_{1B}$ receptor antagonist SSR149415 (also denoted as Nelivaptan) developed by Sanofi-Aventis is a non-peptide $V_{1B}$ receptor antagonist which is orally active (Serradeil-Le Gal et al. (2002); Characterization of (2S, 4R)-1-(5-chloro-1-[(2,4-dimethoxyphenyl)sulfonyl]-3-(2-methoxy-phenyl)-2-oxo-2,3-dihydro-1H-indol-3-yl)-4-hydroxy-N,N-dimethyl-2-pyrrolidine carboxamide (SSR149415), a Selective and Orally Active Vasopressine $V_{1b}$ Receptor Antagonist; WET 300: 1122-1130). SSR149415 is a (2S, 4R)-1-(5-chloro-1-[(2,4-dimethoxyphenyl)sulfonyl]-3-(2-methoxyphenyl)-2-oxo-2, 3-dihydro-1H-indol-3-yl)-4-hydroxy-N,N-dimethyl-2-pyrrolidinecarboxamide having the structural formula

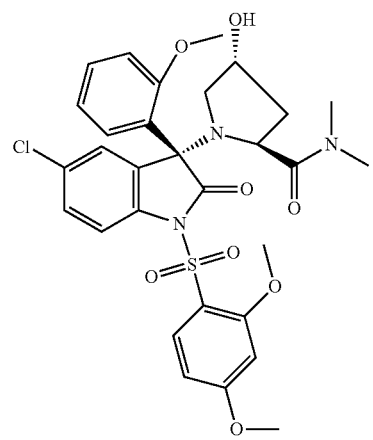 [SMILES: COc1ccc(S(=O)(=O)N2C(=O)[C@@](c3ccccc3OC)(N3C[C@H](O)C[C@H]3C(=O)N(C)C)c3cc(Cl)ccc32)c(OC)c1]

In another specific embodiment the present invention relates to a $V_{1B}$ receptor antagonist for use in the treatment of depressive symptoms and/or anxiety symptoms in a patient showing an elevated AVP level and/or copeptin level, wherein the $V_{1B}$ antagonist is Org 52186. In a further specific embodiment the present invention relates to a $V_{1B}$ receptor antagonist for use in the treatment of depressive symptoms and/or anxiety symptoms in a patient showing an elevated AVP level and/or copeptin level, wherein the $V_{1B}$ receptor antagonist is ABT-436. In another specific embodiment the present invention relates to a $V_{1B}$ receptor antagonist for use in the treatment of depressive symptoms and/or anxiety symptoms in a patient showing an elevated AVP level and/or copeptin level, wherein the $V_{1B}$ receptor antagonist is ABT-558.

In another embodiment of the invention, the patient showing an elevated AVP level and/or an elevated copeptin level is treated with dexamethasone prior to the copeptin measurement or the measurement of AVP. In another embodiment, the patient showing an elevated AVP level and/or an elevated copeptin level is treated with dexamethasone prior to the copeptin measurement and the measurement of AVP.

When one or more combined dexamethasone/corticotropin releasing hormone test(s) (combined dex/CRH test) should subsequently be performed, the blood sample of the patient and/or the sample of the cerebrospinal fluid of the patient may be obtained after the patient has been treated with dexamethasone but before the patient has been treated with CRH.

The patient may be pre-treated with 0.5 mg to 3 mg of dexamethasone, optionally with 0.5 mg, 0.75 mg, 1.0 mg, 1.5 mg, 1.75 mg, 2.0 mg, 2.5 mg, 2.75 mg or 3 mg dexamethasone. In particular, the patient may be pre-treated with 1.5 mg dexamethasone. The blood sample and/or the sample of cerebrospinal fluid may be taken 12 to 36 hours after the patient has been pre-treated with dexamethasone, optionally 15 to 24 hours after the patient has been pre-treated with dexamethasone.

In addition to the copeptin measurement and/or the measurement of AVP, at least one, optionally two combined dexamethasone suppression CRH stimulation test(s) (dex/CRH test) may be performed. If more than one combined dex/CRH test is performed, these tests are performed in certain intervals, e.g. intervals of days, weeks or months. Specifically, the combined dex/CRH tests may be performed in an interval of about 30 or about 60 days. It is however understood, that the length of the interval may be adapted by the person skilled in the art.

The combined dex/CRH test has been described by Heuser et al. (*The combined dexamethasone/CRH test: a refined laboratory test for psychiatric disorders.*, J Psychiatr Res, 1994, 28:341-356) and can be used for screening for compounds which may be useful in the treatment of depressive symptoms and/or anxiety symptoms. The dex/CRH test is described further below with respect to the methods for predicting a treatment response to a $V_{1B}$ receptor antagonist in a patient with depressive symptoms and/or anxiety symptoms according to the invention and it is understood that all aspects of said test as described below are also relevant with respect to the combined dex/CRH test when performed in addition to the copeptin measurement and/or the measurement of AVP.

In another embodiment, the $V_{1B}$ receptor antagonist for use in the treatment of depressive syndromes and/or anxiety syndromes in a patient showing an elevated arginine vasopressin (AVP) level and/or an elevated copeptin level is administered in combination with at least one further pharmaceutically active compound suitable for the treatment of depressive symptoms and/or anxiety symptoms. Pharmaceutically active compounds which may be administered in combination with the $V_{1B}$ receptor antagonist as described herein include in particular compounds labeled for use in the treatment of depressive syndromes and/or anxiety syndromes, compounds currently studied in clinical trials for the treatment of depressive symptoms and/or anxiety symptoms and/or any other compound which is suitable for the treatment of depressive symptoms and/or anxiety symptoms (e.g. use of known compounds not approved by the competent agencies for the treatment of depressive symptoms and/or anxiety symptoms but which are used off-label). It is understood within the meaning of the present invention that each compound mentioned herein may be used in combination with the $V_{1B}$ receptor antagonist for use as described herein either alone or in combination with a further compound mentioned herein.

A non-exhaustive list of compounds suitable for the treatment of depressive symptoms and/or anxiety symptoms includes selective serotonin reuptake inhibitors, serotonin-norepinephrine reuptake inhibitors, dopamine reuptake inhibitors, noradrenergic and specific serotonergic antidepressants, norepinephrine (noradrenaline) reuptake inhibitors, selective serotonin reuptake enhancers, norepinephrine-dopamine disinhibitors, norepinephrine-dopamine reuptake inhibitors, tricyclic antidepressants, tetracyclic antidepressants, monoamine oxidase inhibitors, psychostimulants, mood stabilizers, amine precursors, serotonin antagonist and reuptake inhibitors, anticonvulsants, nicotine, phytopharmaceuticals, melatonin receptor antagonists, 5-HT antagonists, benzodiazepines, buspirone, azapirones, barbiturates, hydroxyzine, pregabalin, corticotropin-releasing hormone receptor antagonists, neurokinin receptor antagonists, oxytocin, glucocorticoid receptor antagonists.

Selective serotonin reuptake inhibitors (SSRIs) are compounds specifically blocking the transporter involved in the reuptake of serotonin and constitute one of the most commonly used class of antidepressants. Examples of SSRIs include citalopram, escitalopram, dapoxetine, fluoxetine, fluvoxamine, paroxetine, sertraline and vilazodone. In one embodiment of the invention the $V_{1B}$ receptor antagonist for use in the treatment of depressive symptoms and/or anxiety symptoms in a patient showing an elevated AVP level and/or an elevated copeptin level as described herein is used in combination with at least one SSRI which is optionally selected from the group consisting of citalopram, escitalopram, dapoxetine, fluoxetine, fluvoxamine, paroxetine, sertraline and vilazodone. The $V_{1B}$ receptor antagonist for use as described herein may be used in combination with one SSRI. Optionally, this SSRI is selected from the group consisting of citalopram, escitalopram, dapoxetine, fluoxetine, fluvoxamine, paroxetine, sertraline and vilazodone. In a specific embodiment, the present invention relates to SSR149415 for use in the treatment of depressive symptoms and/or anxiety symptoms in a patient showing an elevated AVP level and/or an elevated copeptin level used in combination with at least one SSRI, which is optionally selected from the group consisting of citalopram, escitalopram, dapoxetine, fluoxetine, fluvoxamine, paroxetine, sertraline and vilazodone.

Norepinephrine (noradrenaline) reuptake inhibitors (NRIs) exert their activity through blocking the norepinephrine transporter and may also be administered in combination with the $V_{1B}$ receptor antagonist for used as described herein. NRIs as used herein also includes selective norepinephrine reuptake inhibitors as well as NRIs having an activity at a different site. Exemplary NRIs are compounds such as atomoxetin, mazindol, reboxetine, esreboxetin, viloxazine, amedalin, daledalin, CP-39,332, edivoxtin, lortalamine, talopram, talsupram, tandamine, buprorion, ciclazindol and teniloxazine. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one norepinephrine reuptake inhibitor, which is optionally selected from atomoxetin, mazindol, reboxetine, esreboxetin, viloxazine, amedalin, daledalin, CP-39,332, edivoxtin, lortalamine, talopram, talsupram, tandamine, buprorion, ciclazindol and teniloxazine. In a specific embodiment of the invention, the $V_{1B}$ receptor antagonist for use as described herein administered in combination with at least one norephinephrine reuptake inhibitor is SSR149415.

Serotonin-norepinephrine reuptake inhibitors (SNRIs) may also be used for the treatment of depressive symptoms and/or anxiety symptoms. Exemplary SNRIs are desvenlafaxine, duloxetine, milnacipran and venlafaxine. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one SNRI, which is optionally selected from the group consisting of desvenlafaxine, duloxetine, milnacipran and venlafaxine. In a specific embodiment of the invention, the $V_{1B}$ receptor antagonist for use as described herein administered in combination with at least one SNRI is SSR149415.

Dopamine reuptake inhibitors (DRIs, DARIs) are compounds blocking the activity of the dopamine transporter and include selective dopamine reuptake inhibitors as well as other DRIs. Examples of DRIs are amineptine, nomifensine, medifoxamine, methylphenidate, amfonelic acid, benzothiophenylcyclohexylpiperidine (BTCP), as well as *Chaenomeles speciosa*. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one DRI, which is optionally selected from the group consisting of amineptine, nomifensine, medifoxamine, methylphenidate, amfonelic acid, benzothiophenyl-cyclohexylpiperidine (BTCP), as well as *Chaenomeles speciosa*. In a specific embodiment of the invention, the $V_{1B}$ receptor antagonist for use as described herein administered in combination with at least one DRI is SSR149415.

Further compounds which may be administered in combination with the $V_{1B}$ receptor antagonist for use as described herein are noradrenergic and specific serotonergic antidepressants (NaSSAs). Examples of NaSSAs include aptazapine, mianserin and mirtazepin. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one NaSSA which is optionally selected from the group consisting of aptazapine, mianserin and mirtazepin. In a specific embodiment of the invention, the $V_{1B}$ receptor antagonist for use as described herein administered in combination with at least one NaSSA is SSR149415.

Selective serotonin reuptake enhancers such as tianeptine may also be administered in combination with the $V_{1B}$ receptor antagonist for use as described herein. In a specific embodiment of the invention, the $V_{1B}$ receptor antagonist for use as described herein is administered in combination with at least one selective serotonin reuptake enhancer is SSR149415.

Norepinephrine-dopamine disinhibitors denotes a class of compounds inhibiting the release of norepinephrine and dopamine such as agomelatine and may also be used in combination with the $V_{1B}$ receptor antagonist for use as described herein. In a specific embodiment, the $V_{1B}$ receptor antagonist for use as described herein administered in combination with at least one norepinephrine-dopamine disinhibitors is SSR149415.

Norepinephrine-dopamine reuptake inhibitors (NDRIs) are compounds blocking the norepinephrine as well as the dopamine transporter. Exemplary NDRIs are bupropion, pipradrol, dexmethylphenidate, mesocarb, methylphenidatea and pyrovalerone. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one NDRI, which is optionally selected from the group consisting of bupropion, pipradrol, dexmethylphenidate, mesocarb, methylphenidatea and pyrovalerone. In a specific embodiment of the invention, the $V_{1B}$ receptor antagonist for use as described herein administered in combination with at least one NDRI is SSR149415.

Tricyclic antidepressants (TCAs) are cyclic or heterocyclic chemical compounds having three cycles which are useful in the treatment of depressive symptoms and/or anxiety symptoms. Examples of tricylic antidepressants are amineptine, amitriptyline, amytriptylinoxide, butriptyline, clomipramine, demexiptiline, desipramine, dibenzepin, dimetacrine, dosulepin, doxepin, imipramine, imipraminoxide, iprindole, lofepramine, melitracen, metapramine, nitroxazepine, nortriptyline, noxiptiline, opipramol, pipofezine, propizepine, protriptyline, quinupramine, tianeptine and trimipramine. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one TCA, which is optionally selected from the group consisting of amineptine, amitriptyline, amytriptylinoxide, butriptyline, clomipramine, demexiptiline, desipramine, dibenzepin, dimetacrine, dosulepin, doxepin, imipramine, imipraminoxide, iprindole, lofepramine, melitracen, metapramine, nitroxazepine, nortriptyline, noxiptiline, opipramol, pipofezine, propizepine, protriptyline, quinupramine, tianeptine and trimipramine. In a specific embodiment of the invention, the $V_{1B}$ receptor antagonist for use as described herein administered in combination with at least one TCA is SSR149415.

The tetracyclic antidepressants (TeCAs) are also characterized by their chemical structure and are cyclic or heterocyclic compounds having four rings. TeCAs include compounds such as amoxapine, aptazapine, ciclazindol, maprotiline, mianserin, mirtazepine, oxaprotiline and setiptiline. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one TeCA, which is optionally selected from the group consisting of amoxapine, aptazapine, ciclazindol, maprotiline, mianserin, mirtazepine, oxaprotiline and setiptiline. In a specific embodiment of the invention, the $V_{1B}$ receptor antagonist for use as described herein administered in combination with at least one TeCA is SSR149415.

Monoamine oxidase inhibitors (MAOIs) denote compounds blocking the degradation of amines by inhibiting the activity of the enzyme monoamine oxidase. As used herein, MAOIs includes irreversible, reversible and pseudo-irreversible MAOIs as well as compounds selectively inhibiting either monoamine oxidase type A (MAO-A) or monoamine oxidase type B (MAO-B) or showing a non-selective inhibition of MAO. Examplary MAOIs include isocaboxazid, moclobemide, phenelzine, selegiline and trancylcypromine. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one MAOI, which is optionally selected from the group consisting of isocaboxazid, moclobemide, phenelzine, selegiline and trancylcypromine. In a specific embodiment of the invention, the $V_{1B}$ receptor antagonist for use as described herein administered in combination with at least one MAOI is SSR149415.

As used herein, psychostimulants includes any compound which acts stimulating on a body e.g. by improving the mental and/or physical function of the body. Exemplary types of psychostimulants include xanthines, piperazine derivatives and amphetamine derivatives (such as methylphenidate). In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one psychostimulant, which is optionally selected from the group consisting of xanthines, piperazine derivatives and amphetamine derivatives. In a specific embodiment of the invention, the $V_{1B}$ receptor antagonist for use as described herein administered in combination with at least one psychostimulant is SSR149415.

Mood stabilizers which can be used in combination with the $V_{1B}$ receptor antagonist for use as described herein are any compound useful for treatment fast and unstable mood changes. Examples of mood stabilizers include lithium, valproic acid, carbamazepine, lamotrigine, oxacabezipine, riluzole and gabapentin. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one mood stabilizer, which is optionally selected from the group consisting of lithium, valproic acid, carbamazepine, lamotrigine, oxacabezipine, riluzole and gabapentin. In a specific embodiment of the invention, the $V_{1B}$ receptor antagonist for use as described herein administered in combination with at least one mood stabilizer is SSR149415.

Further compounds which may be administered in combination with the $V_{1B}$ receptor antagonist for use as described herein are amine precursors, i.e. metabolic precursors of monoamine neurotransmitter (such as dopamine, noradrenaline, serotonin and acetylcholine). Precursors of monoamine neurotransmitters include L-tryptophan, phenylalanine, 5-hydroxytryptophan, dopamine, L-tyrosine, cholin and L-DOPA. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one amine precursor, which is optionally selected from the group consisting of L-tryptophan, phenylalanine, 5-hydroxytryptophan, dopamine, L-tyrosine, cholin and L-DOPA. In a specific embodiment of the invention, the $V_{1B}$ receptor antagonist for use as described herein administered in combination with at least one amine precursor is SSR149415.

Serotonin antagonists and reuptake inhibitors (SARIs) exert their activity by antagonizing serotonin receptors and include compounds such as nefazodon, etoperidone, lorpiprazole, lubazodone, trazodone and mepiprazole. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one SARI, which is optionally selected from the group consisting of nefazodon, etoperidone, lorpiprazole, lubazodone, trazodone and mepiprazole. In a specific embodiment of the invention, the $V_{1B}$ receptor antagonist for use as described herein administered in combination with at least one SARI is SSR149415.

Anticonvulsant as used herein relates to any compound useful in the treatment and/or prevention of seizures, such as barbiturates, benzodiazepines, carboxamides, valproic acid and hydantoin derivatives. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one anticonvulsant, which is optionally selected from the group consisting of barbiturates, benzodiazepines, carboxamides, valproic acid and hydantoin derivatives. In a specific embodiment of the invention, the $V_{1B}$ receptor antagonist for use as described herein administered in combination with at least one anticonvulsant is SSR149415.

In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with nicotine. In a specific embodiment of the invention, the $V_{1B}$ receptor antagonist for use as described herein administered in combination with nicotine is SSR149415.

Phytopharmaceuticals as used herein includes any composition wherein the active ingredients are solely derived from plants (e.g. from Saint John's wort) and which are useful in the treatment of depressive symptoms and/or anxiety symptoms. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one phytopharmaceutical. In a specific embodiment of the invention, the $V_{1B}$ receptor antagonist for use as described herein administered in combination with at least one phytopharmaceutical is SSR149415.

Compounds useful in the treatment of anxiety symptoms (so-called anxiolytics) include e.g. benzodiazepines, azapirones, barbiturates, pregabalin, hydroxyzine and buspirone. In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one anxiolytic, which is optionally selected from the group consisting of benzodiazepines, azapirones, barbiturates, pregabalin, hydroxyzine and buspirone. In a specific embodiment of the invention, the $V_{1B}$ receptor antagonist for use as described herein administered in combination with at least one anxiolytic is SSR149415.

Further compounds which may be administered in combination with the $V_{1B}$ receptor antagonist for use as described herein include further receptor antagonists such as 5-HT receptor antagonists, melatonin receptor antagonists, corticotropin-releasing hormone (CRH) receptor antagonists, neurokinin receptor antagonists and glucocorticoid receptor antagonists. Optionally, corticotropin-releasing hormone (CRH) receptor antagonists, neurokinin receptor antagonists and glucocorticoid receptor antagonists are administered in combination with the $V_{1B}$ receptor antagonist for use as described herein.

5-HT (5-hydroxytryptamine, serotonin) receptor antagonists as used herein refer to any compound capable of binding directly or indirectly to a 5-HT receptor so as to modulate the receptor mediated activity. Several 5-HT receptor families, i.e. the $5\text{-HT}_1$ receptor family, $5\text{-HT}_2$ receptor family, $5\text{-HT}_3$ receptor family, $5\text{-HT}_4$ receptor family, $5\text{-HT}_5$ receptor family, $5\text{-HT}_6$ receptor family and $5\text{-HT}_7$ receptor family are known in the art, which may be further subdivided in various subtypes. The 5-HT receptor antagonists as used herein may be directed against any of the aforementioned 5-HT receptor families and against any known subtype of these families, in particular against the $5\text{-HT}_2$ family, specifically against the $5\text{-HT}_{2A}$, $5\text{-HT}_{2B}$ and/or $5\text{-HT}_{2C}$ subtype. Exemplary 5-HT receptor antagonists include azapirones ($5\text{-HT}_{1A}$ and $5\text{-HT}_{2A}$ receptor antagonists), aripiprazole ($5\text{-HT}_{2A}$) and agomelatin ($5\text{-HT}_{2C}$ receptor antagonists). In one embodiment of the invention, the $V_{1B}$ receptor antagonist for use in the treatment of depressive symptoms and/or anxiety symptoms in a patient showing an elevated AVP level and/or an elevated copeptin level as described herein is administered in combination with at least one 5-HT receptor antagonist, which is optionally selected from the group consisting of antagonists against the $5\text{-HT}_1$ receptor family, the $5\text{-HT}_2$ receptor family, the $5\text{-HT}_3$ receptor family, the $5\text{-HT}_4$ receptor family, the $5\text{-HT}_5$ receptor family, the $5\text{-HT}_6$ receptor family and the $5\text{-HT}_7$ receptor family. In a specific embodiment of the invention, the $V_{1B}$ receptor antagonist for use as described herein administered in combination with at least one 5-HT receptor antagonist is SSR149415. In a specific embodiment of the invention, the $V_{1B}$ receptor antagonist for use as described herein administered in combination with at least one 5-HT receptor antagonist selected from the group consisting of antagonists against a receptor of the 5-HT$_1$ receptor family, the 5-HT$_2$ receptor family, the 5-HT$_3$ receptor family, the 5-HT$_4$ receptor family, the 5-HT$_5$ receptor family, the 5-HT$_6$ receptor family and the 5-HT$_7$ receptor family is SSR149415.

Melatonin receptor antagonists as used herein refer to any compound capable of binding directly or indirectly to the melatonin receptor so as to modulate the receptor mediated activity. An example of a melatonin receptor antagonist is the melatonergic antidepressant agomelatine. In one embodiment of the invention, the V$_{1B}$ receptor antagonist for use in the treatment of depressive symptoms and/or anxiety symptoms in a patient showing an elevated AVP level and/or an elevated copeptin level as described herein is administered in combination with at least one melatonin receptor antagonist, which is optionally agomelatine. In a specific embodiment of the invention, the V$_{1B}$ receptor antagonist for use as described herein administered in combination with at least one melatonin receptor antagonist is SSR149415.

CRH receptor antagonists as used herein refers to any compound capable of binding directly or indirectly to a CRH receptor 1 or a CRH receptor 2 so as to modulate the receptor mediated activity. CRHR1 antagonists are well known in the literature and are e.g. described in WO 94/13676, EP 0 773 023, WO 2004/047866, WO 2004/094420, WO 98/03510, WO 97/029109, WO 2006/044958, WO 2001/005776 and WO 95/033750. Exemplary CRHR1 antagonists comprise NBI30775/R121919 (Neurocrine), CP316.311 (Pfizer), CP154,526 (Pfizer), Emicerfont (Glaxo), ONO-2333Ms (Ono Pharmaceutical), Pexacerfont (Bristol-Myers-Squibb), SSR125543 (Sanofi-Aventis), NBI-34101 (Neurocrine) and TAI041 (Taisho). In one embodiment of the invention, the V$_{1B}$ receptor antagonist for use in the treatment of depressive symptoms and/or anxiety symptoms in a patient showing an elevated AVP level and/or an elevated copeptin level as described herein is administered in combination with at least one CRH receptor antagonist, particularly a CRHR1 antagonist, which is optionally selected from the group consisting of NBI30775/R121919, CP316.311, CP154,526, Emicerfont, ONO-2333Ms, Pexacerfont, SSR125543, NBI-34101 and TAI041. In another embodiment of the invention, the V$_{1B}$ receptor antagonist for use in the treatment of depressive symptoms and/or anxiety symptoms in a patient showing an elevated AVP level and/or an elevated copeptin level as described herein is administered in combination with at least one CRHR2 receptor antagonist. In a specific embodiment of the invention, the V$_{1B}$ receptor antagonist for use as described herein administered in combination with at least one CRH receptor antagonist is SSR149415.

Neurokinin (NK) receptor antagonists (also known as tachykinin receptor antagonists) as used herein refers to any compound capable of binding directly or indirectly to a neurokinin receptor (e.g. NK$_1$, NK$_2$ or NK$_3$) so as to modulate the receptor mediated activity. In particular, the NK receptor antagonists are NK$_1$ receptor antagonists. Exemplary NK receptor antagonists are the NK$_1$ receptor antagonists vestipitant, L-733,060, Orveptitan, AV608, LY686017, 6R205171, L759274, CPR2721, Casopitant, Aprepitant, the NK$_2$ receptor antagonist saredutant and the NK$_3$ receptor antagonists osanetant and talnetant. In one embodiment of the invention, the V$_{1B}$ receptor antagonist for use in the treatment of depressive symptoms and/or anxiety symptoms in a patient showing an elevated AVP level and/or an elevated copeptin level as described herein is administered in combination with at least one NK receptor antagonist, which is optionally selected from the group consisting of vestipitant, L-733,060, Orveptitan, AV608, LY686017, 6R205171, L759274, CPR2721, Casopitant, Aprepitant, saredutant, osanetant and talnetant. In a specific embodiment of the invention, the V$_{1B}$ receptor antagonist for use as described herein administered in combination with at least one NK receptor antagonist, optionally in combination with at least one NK$_1$ receptor antagonist is SSR149415.

Glucocorticoid receptor antagonists as used herein refers to any compound capable of binding directly or indirectly to a glucocorticoid receptor so as to modulate the receptor mediated activity such as the compounds RU-43044 and RU 38486 (mifepristone). In one embodiment of the invention, the V$_{1B}$ receptor antagonist for use in the treatment of depressive symptoms and/or anxiety symptoms in a patient showing an elevated AVP level and/or an elevated copeptin level as described herein is administered in combination with at least one glucocorticoid receptor antagonist, which is optionally selected from the group consisting of RU-43044 and RU 38486 (mifepristone). In a specific embodiment of the invention, the V$_{1B}$ receptor antagonist for use as described herein administered in combination with at least one glucocorticoid receptor antagonist is SSR149415.

In one embodiment of the invention, the V$_{1B}$ receptor antagonist for use in the treatment of depressive symptoms and/or anxiety symptoms in a patient showing an elevated AVP level and/or an elevated copeptin level as described herein is administered in combination with oxytocin. In a specific embodiment of the invention, the V$_{1B}$ receptor antagonist for use as described herein administered in combination with oxytocin is SSR149415.

The V$_{1B}$ receptor antagonist for use as described herein and the at least one further pharmaceutically active compound may be administered at the same time or at different time points. The V$_{1B}$ receptor antagonist for use as described herein may be administered first, followed by the administration of the at least one pharmaceutically active compound mentioned herein or vice versa. Any sequence of administration of the V$_{1B}$ receptor antagonist for use as described herein and the at least one further pharmaceutically active compound is encompassed in the present invention, e.g. the V$_{1B}$ receptor antagonist for use as described herein may also be administered in between two further pharmaceutically active compounds.

In another embodiment of the use of the V$_{1B}$ receptor antagonist as described herein, a patient showing an elevated AVP level and/or an elevated copeptin level is identified by (i) determining in a patient's sample the status of a biomarker or a group of biomarkers as described herein; and (ii) identifying the patient as eligible for a therapy with a V$_{1B}$ receptor antagonist where the patient's sample is classified as showing the presence or absence of indicator nucleotides as defined herein below.

In another embodiment, a patient showing an elevated AVP level and/or an elevated copeptin level is identified by predicting the patient's treatment response to the V$_{1B}$ receptor antagonist by the prediction methods as described herein below.

In particular, a further aspect of the present invention relates to a method for predicting a treatment response to a V$_{1B}$ receptor antagonist in a patient with depressive symptoms and/or anxiety symptoms, comprising the following steps:
(i) determining the presence or absence of at least one polymorphic variant in the AVPR1B gene in a nucleic acid sample of said patient and
(ii) determining the presence or absence of at least one polymorphic variant in the patient's genome excluding the AVPR1B gene in a nucleic acid sample of said patient, wherein the combination of the presence or absence of at least one polymorphic variant in the AVPR1B gene with the presence or absence of at least one polymorphic variant in the patient's genome excluding the AVPR1B gene is indicative for the treatment response.

The polymorphic variant in the AVPR1B gene and/or in the patient's genome excluding the AVPR1B gene may be a single nucleotide polymorphism (SNP).

The term "determining the presence or absence of a biomarker" or "determining the presence or absence of a polymorphic variant in the AVPR1B gene" or "determining the presence or absence of a polymorphic variant in the patient's genome excluding the AVPR1B gene" as used herein refers to any suitable method or technique of detecting the identity of an SNP, e.g. at the positions of the biomarkers described herein in a sample derived from the patient. The determination method may be a sequencing technique or a technique based on complementary nucleic acid binding. The context of the indicated positions, as well as the strand may differ, e.g. from patient to patient, or from sample to sample etc.

A "nucleic acid sample" or "patient's sample" as used herein may be any sample derived from any suitable part or portion of a subject's body such as a blood sample, a hair sample, a skin sample or a *salvia* sample of the patient from which nucleic acids can be extracted. In some embodiments, blood or saliva samples are used. The sample used in the context of the present invention for detecting the presence of a polymorphic variant or an SNP should be collected in a clinically acceptable manner, in particular in a way that nucleic acids and/or proteins are preserved. Usually, nucleic acid or DNA is extracted or isolated or purified from the sample prior to determining the presence or absence of the polymorphic variants described herein, e.g. in Table 1. Any method known in the art may be used for nucleic acid or DNA extraction or isolation or purification. Suitable methods comprise inter alia steps such as centrifugation steps, precipitation steps, chromatography steps, dialyzing steps, heating steps, cooling steps and/or denaturation steps.

In a specific embodiment of the method described herein, the polymorphic variant in the AVPR1B gene for which the presence or absence is determined is SNP rs28373064 which is represented by a single polymorphic change at position 27 of SEQ ID NO: 2, wherein in one or two alleles of the wild-type nucleotide A is replaced by indicator nucleotide G.

In one embodiment of the invention, the at least one polymorphic variant in the patient's genome excluding the AVPR1B gene for which the presence or absence is determined is selected from the group of biomarkers comprising:
SNP rs9880583 which is represented by a single polymorphic change at position 27 of SEQ ID NO: 3, wherein in one or two alleles the wild-type nucleotide C is replaced by indicator nucleotide G,
SNP rs13099050 which is represented by a single polymorphic change at position 27 of SEQ ID NO: 4, wherein in one or two alleles the wild-type nucleotide A is replaced by indicator nucleotide C,
SNP rs7441352 which is represented by a single polymorphic change at position 27 of SEQ ID NO: 5, wherein in one or two alleles the wild-type nucleotide A is replaced by indicator nucleotide G,
SNP rs730258 which is represented by a single polymorphic change at position 27 of SEQ ID NO: 6, wherein in one or two alleles the wild-type nucleotide C is replaced by indicator nucleotide T,
SNP rs12654236 which is represented by a single polymorphic change at position 27 of SEQ ID NO: 7, wherein in one or two alleles the wild-type nucleotide A is replaced by indicator nucleotide G,
SNP rs17091872 which is represented by a single polymorphic change at position 27 of SEQ ID NO: 8, wherein in one or two alleles the wild-type nucleotide A is replaced by indicator nucleotide G,
SNP rs12254219 which is represented by a single polymorphic change at position 27 of SEQ ID NO: 9, wherein in one or two alleles the wild-type nucleotide C is replaced by indicator nucleotide T,
SNP rs11575663 which is represented by a single polymorphic change at position 27 of SEQ ID NO: 10, wherein in one or two alleles the wild-type nucleotide A is replaced by indicator nucleotide G,
SNP rs7080276 which is represented by a single polymorphic change at position 27 of SEQ ID NO: 11, wherein in one or two alleles the wild-type nucleotide A is replaced by indicator nucleotide G,
SNP rs7416 which is represented by a single polymorphic change at position 27 of SEQ ID NO: 12, wherein in one or two alleles the wild-type nucleotide A is replaced by indicator nucleotide G,
SNP rs12424513 which is represented by a single polymorphic change at position 27 of SEQ ID NO: 13, wherein in one or two alleles the wild-type nucleotide C is replaced by indicator nucleotide T,
SNP rs1035050 which is represented by a single polymorphic change at position 27 of SEQ ID NO: 14, wherein in one or two alleles the wild-type nucleotide C is replaced by indicator nucleotide T,
SNP rs9959162 which is represented by a single polymorphic change at position 27 of SEQ ID NO: 15, wherein in one or two alleles the wild-type nucleotide A is replaced by indicator nucleotide C, and/or
SNP rs8088242 which is represented by a single polymorphic change at position 27 of SEQ ID NO: 16, wherein in one or two alleles the wild-type nucleotide A is replaced by indicator nucleotide G.

A further embodiment of the present invention relates to the method described herein, wherein the at least one polymorphic variant in the AVPR1B gene and/or in the patient's genome excluding the AVPR1B gene for which the presence or absence is determined is selected from a set/group of biomarkers comprising at least 2, at least 5, at least 8 or at least 11 of the markers as defined in Table 1. In one embodiment, the at least one polymorphic variant in the AVPR1B gene and/or in the patient's genome excluding the AVPR1B gene for which the presence or absence is determined is selected from a set or group of biomarkers consisting of the biomarkers as defined in Table 1.

In another embodiment, the combination of the presence or absence of SNP rs28373064 with the presence or absence of at least 1, at least 2, at least 3, at least 4, at least 5, at least 6, at least 7, at least 8, at least 9, at least 10, at least 11, at least 12, at least 13 or at least 14 polymorphic variants in the patient's genome excluding the AVPR1B gene as defined in Table 1 (excluding SNP rs28373064) is determined.

In yet another embodiment, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 is indicative for a treatment response to a $V_{1B}$ receptor antagonist. In yet another embodiment the absence of SNP rs28373064 in combination with the absence of SNP rs13099050, SNP rs7441352 and SNP rs12424153 is indicative for a treatment response to a $V_{1B}$ receptor antagonist. In one embodiment, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 and the absence of SNP rs28373064 in combination with the absence of SNP rs13099050, SNP rs7441352 and SNP rs12424153 is indicative for a treatment response to a $V_{1B}$ receptor antagonist. It is however to be understood that the analysis of other factors, such as the gender of the patient and the presence or absence of each of the SNPs defined in Table 1 may further add to the prediction analysis for the treatment response to a $V_{1B}$ receptor antagonist.

It is understood that additionally the presence of one or more further marker(s), such as clinical markers may be determined in addition to the presence of the herein-described markers. Such clinical markers may include the AVP and/or copeptin level.

According to the method described herein, the presence or absence of the polymorphic variant in the AVPR1B gene and the presence or absence of the one or more further markers may determined by single nucleotide polymorphism genotyping analysis. The term "single nucleotide polymorphism (SNP) genotyping analysis" as used herein refers to a test of determining in one or several patients the presence or absence of at least one SNP, typically several SNPs, and in some embodiments all (known) SNPs the human genome, including endogenous and exogenous regions.

For example, the determination of the nucleotide sequence and/or molecular structure may be carried out through allele-specific oligonucleotide (ASO)-dot blot analysis, primer extension assays, iPLEX SNP genotyping, Dynamic allele-specific hybridization (DASH) genotyping, the use of molecular beacons, tetra primer ARMS PCR, a flap endonuclease invader assay, an oligonucleotide ligase assay, PCR-single strand conformation polymorphism (SSCP) analysis, quantitative real-time PCR assay, SNP microarray based analysis, restriction enzyme fragment length polymorphism (RFLP) analysis, targeted resequencing analysis and/or whole genome sequencing analysis.

SNP genotyping analysis can be performed by methods known in the art such as microarray analysis or sequencing analysis or PCR related methods or mass spectrometry or 5'-nuclease assays or allele specific hybridization or high-throughput variants of these techniques or combinations thereof. These and other methods are known in the art. See for example Rampal, DNA Arrays: Methods and Protocols (Methods in Molecular Biology) 2010; Graham & Hill, DNA Sequencing Protocols (Methods in Molecular Biology) 2001; Schuster, Nat. Methods, 2008 and Brenner, Nat. Biotech., 2000; Mardis, Annu Rev Genomics Hum Genet., 2008. Genomewide arrays can be purchased from different suppliers such as Illumia and Affymetix.

In another embodiment of the present invention, a patient showing an elevated AVP level and/or an elevated copeptin level can be identified by (i) determining in a patient's sample the status of a biomarker or a group of biomarkers as defined above; and (ii) identifying the patient as eligible for a therapy with a $V_{1B}$ receptor antagonist, where the algorithm provided by the method described below predicts that the patient responds to the treatment with $V_{1B}$ receptor antagonist.

One aspect of the invention thus concerns the provision of such an algorithm for predicting a treatment response to $V_{1B}$ receptor antagonists in patients with depressive symptoms and/or anxiety symptoms. The method may comprise the following steps:

(a) performing a single nucleotide polymorphism (SNP) genotyping analysis in a group of patients with depressive symptoms and/or anxiety symptoms;

(b) determining a value indicative for CRH activity in each patient of the group, wherein a value indicative for CRH overactivity is indicative or predictive for a patient responding to a treatment with a $V_{1B}$ receptor antagonist;

(c) determining whether the presence or absence of at least one SNP and combination of the presence or absence of at least two SNPs is associated with a value indicative for CRH overactivity as determined in step (b);

(d) determining the algorithm by machine-learning from the association of the at least one SNP identified in step (c) with the value indicative for CRH overactivity and the association of the interactions of at least two SNPs identified in step (c) with a value indicative for CRH overactivity.

In a step (a), a single nucleotide polymorphism (SNP) genotyping analysis in a group of patients with depressive symptoms and/or anxiety symptoms is performed.

A "group of patients" as used herein comprises at least two patients, such as at least 10 patients, or at least 100 patients, or at least 150 patients. Patients included in the analysis of step (a) may exhibit at least a moderate to severe depressive mode. The group of patients may comprise patients with CRH overactivity and/or patients with normal CRH activity.

SNP genotyping analysis can be performed by methods known in the art such as the methods mentioned herein.

In some embodiments, any of the methods described herein comprises the determination of the haplotype for two copies of the chromosome comprising the SNPs identified herein.

Typically, a SNP is considered in the genotyping analysis if it occurs in a certain percentage in the population, for example in at least 5% or at least 10% of the population. In other words, the minor allele frequency (MAF) is larger than 0.05 or 0.10 (MAF>0.05 or MAF>0.10).

For the SNP genotyping analysis a nucleic acid or DNA sample from a patient may be used. The nucleic acid or DNA sample can be a blood sample, a hair sample, a skin sample or a *salvia* sample of the patient. Any other sample obtainable from the patient and containing patient nucleic acid or DNA can also be used. The sample can be collected from the patient by any method known in the art. For example, a blood sample can be taken from a patient by use of a sterile needle. The collection of salvia out of the mouth and throat of the patient can be performed by use of a sterile cotton bud or by flushing said area and collecting the flushing solution.

Usually, the nucleic acid or DNA is extracted or isolated or purified from the sample prior to SNP genotyping analysis. Any method known in the art may be used for nucleic acid or DNA extraction or isolation or purification. Suitable methods comprise inter alia steps such as centrifugation steps, precipitation steps, chromatography steps, dialyzing steps, heating steps, cooling steps and/or denaturation steps. For some embodiments, a certain nucleic acid or DNA content in the sample may be reached. Nucleic acid or DNA content can be measured for example via UV spectrometry as described in the literature. However, in alternative embodiments SNP genotyping analysis may also be performed by using a non-extracted or non-purified sample.

Nucleic acid or DNA amplification may also be useful prior to the SNP analysis step. Any method known in the art can be used for nucleic acid or DNA amplification. The sample can thus be provided in a concentration and solution appropriate for the SNP analysis.

The analyzed SNPs may be represented by values 0, 1 or 2. The value "0" may indicate that the SNP is present on none of the two homologous chromosomes. The value "1" may indicate that the SNP is present on one of the two homologous chromosomes. The value "2" may indicate that the SNP is present on both homologous chromosomes. Homologous chromosomes correspond to each other in terms of chromosome length, gene loci and staining pattern. One is inherited from the mother, the other from the father.

In a step (b) of the method for providing a prediction algorithm, a value indicative for CRH activity in each patient is determined.

A "value indicative for CRH activity", a "value indicative for CRH overactivity" and/or a "value indicative for normal CRH activity" can be obtained by determining the concentration or activity of CRH and/or of a downstream target of the CRHR1 receptor. The analysis is usually set up in a way that it can be excluded that the modulation of activity or concentration of a downstream target of the CRHR1 receptor is due to another disturbance than CRH activity. For instance, the concentrations or activities of adrenocorticotrophin (ACTH) and/or cortisol are useful biomarkers for determining a value indicative for CRH overactivity. Typically, the CRH overactivity in each patient may be determined by measuring the ACTH and/or cortisol level response to a combined dexamethasone suppression/CRH stimulation test as described herein.

Steps (c) and (d) of the method for providing a prediction algorithm may analyze the association of the analyzed SNPs with the value indicative for CRH overactivity and/or normal CRH activity and generate an algorithm for predicting the treatment response to $V_{1B}$ receptor antagonists. In addition or alternatively, steps (c) and (d) of the method for providing a prediction algorithm may analyze the association of a combination of the presence or absence of at least two of the analyzed SNPs, in particular a combination of the presence or absence of at least one SNP in the AVPR1B gene with the presence or absence of at least one SNP in the genome of the patient excluding the AVPR1B gene with a value indicative for CRH overactivity and/or normal CRH activity and generate an algorithm for predicting the treatment response to $V_{1B}$ receptor antagonists. Additionally, steps (c) and (d) of the method for providing a prediction algorithm may analyze the association of the gender of the patient from which the sample was derived with a value indicative for CRH overactivity and/or normal CRH activity and generate an algorithm for predicting the treatment response to $V_{1B}$ receptor antagonists.

In an exemplary embodiment, the group of patients may be split into two sets of similar size and similar values for descriptors such as demographic descriptors or clinical descriptors. These two sets are hereinafter also referred to as "training set" and "test set".

In step (c) of the method of this exemplary embodiment, at least one SNP associated with the value indicative for CRH overactivity and/or normal CRH activity as determined in step (b) is identified in the training set. In addition or alternatively, in step (c) the association of a combination of the analyzed SNPs with a value indicative for CRH overactivity and/or normal CRH activity as determined in step (b) may be identified in the training set. Optionally, in step (c) the association of the gender of the patient from which the sample was derived with a value indicative for CRH overactivity and/or normal CRH activity as determined in step (b) is identified in the training set.

Further, there can be at least two alternatives for the result provided by the prediction algorithm. First, the result may be a categorical answer whether the patient responds to $V_{1B}$ receptor antagonist treatment or not. Second, the prediction algorithm may provide the answer to which degree the patient responds or does not respond to the treatment. Depending on the desired result provided by the prediction algorithm the way of determining the algorithm may differ.

In the alternative the prediction algorithm will analyze whether a patient responds or does not respond to $V_{1B}$ receptor antagonist treatment, the values indicative for CRH activity may be provided as logic data variable (Boolean type; 0 vs. 1; true vs. false, high vs. low responder). Therefore, if the test performed to determine values indicative for CRH overactivity provides a data range, the patients may be dichotomized by a threshold into high vs. low responders.

In the alternative the test will analyze to which degree or likelihood the patient may respond or may not respond to $V_{1B}$ receptor antagonist treatment, the values indicative for CRH activity may be provided as numerical values.

Typically, SNPs that are modified in a significant percentage of the population are used in the method for providing a prediction algorithm. For example, only SNPs with a minor allele frequency (MAF) greater than 0.05 or 0.10 may be selected for further analysis. This means that only SNPs that are modified in at least 5% or 10% of the population are selected for further analysis.

Association for all SNPs or combinations of SNPs with the value indicative for CRH activity is tested by an association analysis testing the likelihood for a patient to be CRH overactive vs. CRH non-overactive in dependence of the genotype of said patient. Said association analysis may be conducted for example by an additive genetic model and/or by a logistic regression. A SNP or combination of at least two SNPs is e.g. identified to be associated with a value indicative for CRH overactivity if the corresponding p-value is at least $1\times10^{-3}$ or at least $1\times10^{-4}$ or at least $1\times10^{-5}$. The lower the p-value the more the SNP is associated with a value indicative for CRH overactivity. Accordingly, an SNP or combination of at least two SNPs is e.g. identified to be associated with a value indicative for normal CRH activity if the corresponding p-value is at least $1\times10^{-3}$ or at least $1\times10^{-4}$ or at least $1\times10^{-5}$. In one embodiment of the invention, only SNPs or combinations of SNPs with a p-value of $<1\times10^{-5}$ are used.

In step (d) of this exemplary embodiment, the algorithm for predicting a treatment response to $V_{1B}$ receptor antagonist may be determined by the use of SNPs or combinations of SNPs in the test set by a machine learning method.

The term "algorithm for predicting" as used herein may refer to a classification function (also known as binary classification test).

The term "machine-learning" as used herein may refer to a method known to the person skilled in the art of machine learning. In particular, machine learning is concerned with the design and development of algorithms that allow computers to evolve behaviors based on empirical data, such as from sensor data or databases. It may be selected from the group consisting of artificial neural network learning, decision tree learning, support vector machine learning, Bayesian network learning, clustering, and regression analysis.

The term "reliable prediction of the treatment response to a $V_{1B}$ receptor antagonist" as used herein may refer to a high performance of the prediction algorithm. The evaluation of the performance of the prediction algorithm may depend on the problem the algorithm is applied for. If the algorithm is used to identify patients that are likely to response to the treatment with $V_{1B}$ receptor antagonists the performance is usually expressed by a high accuracy and/or sensitivity and/or precision. If patients should be identified which are likely not to respond to the treatment with $V_{1B}$ receptor antagonist, specificity and/or negative predictive value are typical statistical measures to describe the performance of the prediction algorithm.

For optimizing the prediction performance of the algorithm, the step of determining the algorithm by a machine-learning method in a first subset of the test set and testing the prediction performance in an second independent subset of the test set may be repeated based on different numbers and groups of SNPs, until the desired prediction performance is reached.

Accuracy, sensitivity, precision, specificity and negative predictive value are exemplary statistical measure of the performance of the prediction algorithm. In the following, examples are given for determining the performance of the prediction algorithm.

As used herein, accuracy may be calculated as (number of true positives+number of true negatives)/(number of true positives+number of false positives+number of true negatives+number of false negatives), e.g. (number of patients correctly diagnosed as responding to $V_{1B}$ receptor antagonist+number of patients correctly diagnosed as not responding to $V_{1B}$ receptor antagonist)/(number of patients correctly diagnosed as responding to $V_{1B}$ receptor antagonist+number of patients wrongly diagnosed as responding to $V_{1B}$ receptor antagonist+number of patients correctly diagnosed as not responding to $V_{1B}$ receptor antagonist+number of patients wrongly diagnosed as not responding to $V_{1B}$ receptor antagonist). The accuracy of prediction may e.g. be at least 60%, at least 70%, at least 80% or at least 90%.

A used herein, sensitivity may be calculated as (true positives)/(true positives+false negatives), e.g.: (number of patients correctly diagnosed as responding to $V_{1B}$ receptor antagonist)/(number of patients correctly diagnosed as responding to $V_{1B}$ receptor antagonist+number of patients wrongly diagnosed as not responding to $V_{1B}$ receptor antagonist). The sensitivity of prediction may be at least 60%, at least 70%, at least 80% or at least 90%.

As used herein, precision (also referred to as positive predictive value) may be calculated as (true positives)/(true positives+false positives), e.g.: (number of patients correctly diagnosed as responding to $V_{1B}$ receptor antagonist)/(number of patients correctly diagnosed as responding to $V_{1B}$ receptor antagonist+number of patients wrongly diagnosed as responding to $V_{1B}$ receptor antagonist). The precision of prediction may be at least 60%, at least 70%, at least 80% or at least 90%.

As used herein, specificity is calculated as (true negatives)/(true negatives+false positives), e.g.: (number of patients correctly diagnosed as not responding to $V_{1B}$ receptor antagonist)/(number of patients correctly diagnosed as not responding to $V_{1B}$ receptor antagonist+number of patients wrongly diagnosed as not responding to $V_{1B}$ receptor antagonist). The specificity of prediction may be at least 60%, at least 70%, at least 80% or at least 90%.

As used herein, negative predictive value is calculated as (true negatives)/(true negatives+false negatives), e.g.: (number of patients correctly diagnosed as not responding to $V_{1B}$ receptor antagonist)/(number of patients correctly diagnosed as not responding to $V_{1B}$ receptor antagonist+number of patients wrongly diagnosed as not responding to $V_{1B}$ receptor antagonist). The negative predictive value may be at least 60%, at least 70%, at least 80% or at least 90%.

Other statistical measures useful for describing the performance of the prediction algorithm are geometric mean of sensitivity and specificity, geometric mean of positive predictive value and negative predictive value, F-measure and area under ROC curve, and the positive and negative likelihood ratios, the false discovery rate and Matthews correlation coefficient. These measures and method for their determination are well known in the art.

In general, a prediction algorithm with high sensitivity may have low specificity and vice versa. The decision to select an algorithm having certain statistical characteristics such as accuracy, sensitivity or specificity may also depend on the costs associated with a treatment with a $V_{1B}$ receptor antagonist should the prediction be positive and/or whether such a treatment is detrimental in cases where the result is a false positive.

For a prediction whether a patient likely responds to the treatment with $V_{1B}$ receptor antagonists the prediction algorithm may be based on a number of SNPs and/or combinations of SNPs sufficient to achieve a prediction sensitivity and/or precision of at least 55%, optionally at least 80%.

For the prediction whether it is unlikely that a patient responds to the treatment with $V_{1B}$ receptor antagonists the prediction algorithm may be based on a number of SNPs and/or combinations of SNPs sufficient to achieve a prediction specificity and/or negative predictive value of at least 55%, optionally at least 80%.

For a prediction whether a patient responds to a treatment with $V_{1B}$ receptor antagonists or not the prediction algorithm may be based on a number of SNPs and/or combinations of SNPs sufficient to achieve sensitivity and/or precision and/or specificity and/or negative predictive value of at least 55%, optionally at least 80%.

In one embodiment, a number N of SNPs and/or combinations of SNPs is associated with a value indicative for CRH overactivity or normal CRH activity in step (c) of the method for providing an algorithm, wherein N is sufficient to provide an accuracy of at least 80% and a sensitivity of at least 70% and a specificity of at least 70%. In another embodiment, N is sufficient to provide an accuracy of at least 85% and a sensitivity of at least 80% and a specificity of at least 80%. In one embodiment, a sufficient number N of SNPs and/or combinations of SNPs comprises at least one polymorphic variant in the AVPR1B gene in combination with a set or group of polymorphic variants in the patient's genome excluding the AVPR1B gene, e.g. to a combination of a polymorphic variant in the AVPR1B gene, optionally SNP rs28373064, with at least 1, at least 2, at least 3, at least 4, at least 5, at least 6, at least 7, at least 8, at least 9, at least 10, at least 11, at least 12, at least 13, or at least 14 polymorphic variant(s) as described herein for polymorphic variants in the patient's genome excluding the AVPR1B gene.

In another embodiment, the presence or absence of a number M of SNPs and/or combinations of SNPs is determined in step (a) of the method for predicting a treatment response, wherein M is sufficient to provide an accuracy of at least 80% and a sensitivity of at least 70% and a specificity of at least 70%. In another embodiment, M is sufficient to provide an accuracy of at least 85% and a sensitivity of at least 80% and a specificity of at least 80%. In one embodiment, a sufficient number M of SNPs and/or combinations of SNPs comprises at least one polymorphic variant in the AVPR1B gene in combination with a set or group of polymorphic variants in the patient's genome excluding the AVPR1B gene, e.g. to a combination of a polymorphic variant in the AVPR1B gene, optionally SNP rs28373064, with at least 1, at least 2, at least 3, at least 4, at least 5, at least 6, at least 7, at least 8, at least 9, at least 10, at least 11, at least 12, at least 13, or at least 14 polymorphic variant(s) as described herein for polymorphic variants in the patient's genome excluding the AVPR1B gene.

Typically, at least 2, at least 5, at least 8 or at least 11 SNPs and/or combinations of SNPs are used for determination of the algorithm in step (d) of the method for providing a prediction algorithm.

The skilled person in the art knows that the use of different machine-learning methods and adapting parameters used therein can be also used for improvement of the prediction reliability. The whole statistical work-flow can be automated by a computer.

Thus, in one embodiment the method for predicting a treatment response to a $V_{1B}$ receptor antagonists further comprises a step (iii), wherein the treatment response to $V_{1B}$ receptor antagonists is predicted by linking the algorithm provided by the method for providing a prediction algorithm with the presence or absence of at least one SNP and combination of SNPs as determined in step (i) and (ii) of said method. In particular, said SNPs correspond to the SNPs shown herein in Table 1 and the combinations of SNPs described herein.

"Linking an algorithm for predicting a treatment response to $V_{1B}$ receptor antagonist in patients having depressive symptoms and/or anxiety symptoms with the presence or absence of the at least one SNP and/or combination of SNPs" as used herein may refer to using such an algorithm to predict the treatment response based on the determined presence or absence of the at least one SNP and/or combination of SNPs, e.g. by integrating the at least one SNP and/or combination of SPCs determined in step (a) of the above method by the algorithm. In one embodiment, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 may be integrated by the algorithm. In another embodiment the absence of SNP rs28373064 in combination with the absence of SNP rs13099050, SNP rs7441352 and SNP rs12424153 may be integrated by the algorithm. In particular, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 and the absence of SNP rs28373064 in combination with the absence of SNP rs13099050, SNP rs7441352 and SNP rs12424153 may be integrated by the algorithm. As already mentioned above, further factors, such as the gender of the patient and the presence or absence of the SNPs defined herein in Table 1 may also be integrated by the algorithm.

Another aspect of the invention relates to a method for predicting a treatment response to a $V_{1B}$ receptor antagonist in a patient with depressive symptoms and/or anxiety symptoms, wherein the copeptin concentration in a blood sample of said patient is determined and/or the AVP concentration in a sample of cerebrospinal fluid of said patient is determined and wherein an elevated copeptin and/or an elevated AVP concentration is indicative for a patient responding to a treatment with a $V_{1B}$ receptor antagonist.

In particular, another aspect of the present invention relates to a method for predicting a treatment response to a $V_{1B}$ receptor antagonist in a patient with depressive symptoms and/or anxiety symptoms, wherein the copeptin concentration in a blood sample of said patient is determined or the AVP concentration in a sample of cerebrospinal fluid of said patient is determined and wherein the presence of an elevated copeptin or an elevated AVP concentration is indicative for a patient responding to a treatment with a $V_{1B}$ receptor antagonist.

Another aspect of the present invention relates to a method for predicting a treatment response to a $V_{1B}$ receptor antagonist in a patient with depressive symptoms and/or anxiety symptoms, wherein both the copeptin concentration in a blood sample of said patient is determined and the AVP concentration in a sample of cerebrospinal fluid of said patient are determined and wherein the presence of both, an elevated copeptin and an elevated AVP concentration is indicative for a patient responding to a treatment with a $V_{1B}$ receptor antagonist.

The patient may be a patient showing depressive symptoms. Alternatively, the patient may be a patient showing anxiety symptoms. Alternatively, the patient may be a patient showing both, depressive and anxiety symptoms.

The term "treatment response to a $V_{1B}$ antagonist in patients with depressive symptoms and/or anxiety symptoms" in the sense of the invention refers to a response in a patient with depressive symptoms and/or anxiety symptoms during and/or after the treatment with one or more $V_{1B}$ antagonists compared to the state before the treatment. The response may range from a partial alleviation of the symptoms to a complete remission of the symptoms, indicated by the change of symptoms strength and/or frequency of relapse of individual symptoms and/or the mean change on a depression scale, e.g. as described herein. The response can occur shortly after treatment or after a certain time period. A decrease in symptom severity from pre-treatment of 25% or more is usually considered a partial alleviation of symptoms. Remission may be defined as achieving a value of 8 or less on the Hamilton Depression Rating Scale (HAM-D) or equivalent values on other rating scales named herein.

The blood sample and the sample of cerebrospinal fluid can be obtained from the patient by any method known in the art. For example, a blood sample can be taken from a patient by use of a sterile needle and a cerebrospinal fluid sample can be taken by lumbar puncture. It is also understood that all steps necessary for preparing the sample for the respective measurement are also encompassed in the method according to the invention. Such preparation steps include e.g. the preparation of the blood sample in order to obtain blood plasma as described above and are known to the person skilled in the art.

In a specific embodiment of the method described herein, the blood sample of the patient and/or the sample of the cerebrospinal fluid of the patient is/are taken after the patient has been treated with dexamethasone. Subsequently, the copeptin concentration in the blood sample and/or the AVP concentration in the sample of cerebrospinal fluid of said patient is/are determined.

When at least one combined dexamethasone/corticotropin releasing hormone test (combined dex/CRH test) should subsequently be performed, the blood sample of the patient and/or the sample of the cerebrospinal fluid of the patient may be obtained after the patient has been treated with dexamethasone but before said patient has been treated with CRH in the course of each combined dex/CRH test.

The patient may be pre-treated with 0.5 mg to 3 mg of dexamethasone, optionally with 0.5 mg, 0.75 mg, 1.0 mg, 1.5 mg, 1.75 mg, 2.0 mg, 2.5 mg, 2.75 mg or 3 mg dexamethasone. In particular, the patient may be pre-treated with 1.5 mg dexamethasone. The blood sample may be taken 12 to 36 hours after the patient has been treated with dexamethasone, optionally 15 to 24 hours after the patient has been treated with dexamethasone.

In one embodiment of the method for predicting a treatment response to a $V_{1B}$ receptor antagonist in a patient with depressive symptoms and/or anxiety symptoms as described herein the patient is additionally subjected to at least one combined dexamethasone suppression CRH stimulation test (dex/CRH test). When more than one combined dex/CRH test is performed, these tests are performed in certain intervals, e.g. intervals of days, weeks or months. Optionally, the patient is subjected to at least one, particular two combined dex/CRH tests, whereby the tests are performed in an interval of about 30 days or of about 60 days. It is however understood that the length of the interval between the tests may be adapted as considered necessary by the person skilled in the art.

The combined dex/CRH test has been described by Heuser et al. (*The combined dexamethasone/CRH test: a refined laboratory test for psychiatric disorders*., J Psychiatr Res, 1994, 28:341-356) and can be used for screening for compounds which may be useful in the treatment of depressive symptoms and/or anxiety symptoms. In detail, in the combined dex/CRH test subjects are pre-treated with dexamethasone (e.g. 1.5 mg dexamethasone) and blood is drawn in certain intervals after the dexamethasone treatment. This blood sample shows the suppression of cortisol by dexamethasone. The pre-treatment is normally performed in the evening prior to the day of the CRH administration. Human CRH (e.g. 100 μg CRH) is administered after the first pre-treatment with dexamethasone, e.g. 16 hours after the pre-treatment. Subsequently, blood samples are drawn (e.g. in intervals of 15 minutes) from the patient and the plasma ACTH and/or cortisol concentrations are determined. The neuroendocrine response to the dex/CRH test may be analyzed using the total area under the curve (AUC) of the ACTH response. Patients suffering from depression normally show an increased release of cortisol and of adrenocorticotropic hormone (ACTH) in response to the combined treatment with dexamethasone and CRH as performed during the test, thus indicating a dysregulation of the hypothalamic-pituitary-adrenal (HPA) axis. Patients with a high HPA axis dysregulation show AUC values of cortisol of between 3000 and 18000 AUC units (ng/ml×75 min) and/or AUC values of ACTH of between 1000 and 6500 AUC units (pg/ml×75 min). Patients having a low HPA axis dysregulation show AUC values of cortisol of between 300 and 2500 AUC units (ng/ml×75 min) and/or AUC values of ACTH of between 250 and 1000 AUC units (pg/ml×75 min) Various antidepressants lead to a reduction of these increased cortisol and ACTH levels in a combined dex/CRH test performed after the treatment with the antidepressants. Treatment response to antidepressants can thus be determined by performing a second dex/CRH test after treatment with the antidepressant and comparing the neuroendocrine response to the one shown in a combined dex/CRH test performed prior to treatment with the antidepressant.

In one embodiment of the present method for predicting a treatment response to a $V_{1B}$ receptor antagonist in a patient with depressive symptoms and/or anxiety symptoms as described herein, an elevated AVP level in said patient is determined by means of AVP measurement in a sample of cerebrospinal fluid of said patient. Samples of cerebrospinal fluid can be obtained from the patient by any method known in the art, e.g. by lumbar puncture.

Methods for determination of AVP levels in a sample of cerebrospinal fluid of a patient are known in the art and include immunoassays, e.g. radioimmunoassays. Hence, in another embodiment of the invention the AVP level in the sample of cerebrospinal fluid of the patient is measured by means of immunoassay, optionally by means of radioimmunoassay.

As used herein, an elevated AVP level denotes any AVP level higher than the AVP level measured in blood samples and/or samples of the cerebrospinal liquid of healthy individuals. Specifically, an elevated AVP level in a patient showing depressive symptoms and/or anxiety symptoms is indicated by an AVP concentration in the sample of cerebrospinal fluid of at least 4 pg/ml AVP, least 5 pg/ml AVP, least 6 pg/ml AVP, least 7 pg/ml AVP, least 8 pg/ml AVP, at least 10 pg/ml AVP, at least 20 pg/ml AVP, at least 30 pg/ml AVP, at least 50 pg/ml AVP, at least 70 pg/ml AVP or at least 90 pg/ml AVP. Elevated AVP levels may be indicated by an AVP concentration in the sample of cerebrospinal fluid in the range from 4 to 8 pg/ml AVP, optionally in the range from 4 to 6 pg/ml AVP. Such elevated AVP concentrations are indicative for a patient responding to a treatment with a $V_{1B}$ receptor antagonist as described herein.

In a further embodiment, the present invention relates to method for predicting a treatment response to a $V_{1B}$ receptor antagonist in a patient with depressive symptoms and/or anxiety symptoms as described herein, wherein an elevated AVP level and/or an elevated copeptin level in said patient is determined by means of copeptin measurement.

Methods for determination of copeptin levels in a blood sample derived from a patient are known in the art and include immunoassays, e.g. sandwich immunoassays. Examples of such immunoassays are the Copeptin EIA Kit provided by BioSupply UK, the Thermo Scientific B R A H M S copeptin Kryptor assay and the Thermo Scientific B R A H M S copeptin Kryptor us assay provided by Thermo-Scientific.

Hence, in another embodiment of the method according to the invention, the AVP level and/or copeptin level of the patient showing depressive symptoms and/or anxiety symptoms is determined by means of an immunoassay, optionally by means of a sandwich immunoassay. According to the method of the invention, the copeptin level is determined in a blood sample of the patient as defined herein. The blood sample can be obtained from the patient by any method known in the art, e.g. with a sterile needle. In a specific embodiment of the invention, the copeptin level is determined in the blood plasma derived from the blood sample of said patient. It is known in the art that blood plasma may be derived by centrifugation of a blood sample to which an anti-coagulant has been added.

As used herein, an elevated copeptin level denotes any copeptin level higher than the copeptin level measured in blood samples of healthy individuals. Specifically, an elevated copeptin level and therefore also an elevated AVP level in a patient showing depressive symptoms and/or anxiety symptoms is indicated by a copeptin blood concentration of at least 5 pmol/L, at least 6 pmol/L, at least 7 pmol/L, at least 8 pmol/L, at least 9 pmol/L, at least 10 pmol/ml, at least 20 pmol/ml, at least 30 pmol/ml, at least 40 pmol/ml, at least 50 pmol/ml, at least 60 pmol/ml, at least 70 pmol/ml, at least 80 pmol/ml, at least 90 pmol/ml or at least 100 pmol/ml. Elevated copeptin levels and therefore also elevated AVP levels may be indicated by a copeptin blood concentration in the range from 5 to 9 pmol/L, optionally in the range from 5 to 7 pmol/L. Such elevated copeptin levels are indicative for a patient responding to a treatment with a $V_{1B}$ receptor antagonist as described herein.

It is also encompassed in the invention that both, the elevated copeptin level in a blood sample of the patient and the elevated AVP level in a sample of cerebrospinal fluid of the patient is determined in the patient by means of copeptin measurement and measurement of AVP in order to predict the treatment response to a $V_{1B}$ receptor antagonist.

The methods described above are not restricted to methods predicting a treatment response to $V_{1B}$ antagonists in patients with depressive symptoms and/or anxiety symptoms. The treatment response of patients with depressive symptoms and/or anxiety symptoms to a combined administration of a $V_{1B}$ receptor antagonist as described herein and a further pharmaceutically active compound suitable in the treatment of depressive symptoms and/or anxiety symptoms as described herein may also be predicted by the methods described herein. Furthermore, the treatment response to any other compound, drug or biomolecule that is capable of treating depressive symptoms and/or anxiety symptoms in patients who have an elevated arginine vasopressine (AVP) level and/or elevated copeptin level may be also be predicted by methods described herein. In particular, the disclosure can be understood to mean that the term "$V_{1B}$ receptor antagonists" can be replaced by any other compound that interferes with the $V_{1B}$ receptor mediated pathway and leads to a reduction and/or remission of depressive symptoms and/or anxiety symptoms patients with elevated arginine vasopressine (AVP) level and/or elevated copeptin level.

The invention is further described in the following examples which are solely for the purpose of illustrating specific embodiments of the invention, and are also not to be construed as limiting the scope of the invention in any way.

EXAMPLES

Example 1

Sample Description

Patients participating in the Munich Antidepressant Response Signature (MARS) project have been included. Selection criteria were:

150 inpatients suffering from unipolar major depression, who were divided into 75 patients with high vs. low HPA axis dysregulations, each, using matched extremes according to the results of a combined dex/CRH test at the time of admission 123 inpatients with two consecutive dex/CRH tests during hospitalisation, the first at admission, the second on average 60 days thereafter Due to partial overlap between patients selected according to the two criteria, the total number of subjects included in this analysis is 202. Copeptin was measured in the plasma samples of the combined dex/CRH test using the first specimen, which was obtained under dex suppression, but prior to CRH stimulation.

Associations Between Copeptin and Dex/CRH Test Outcome

Patients of the MARS project have been divided into 75 with high and 75 with low HPA axis dysregulations according to the results of a first combined dex/CRH test, which was conducted on average 6 days after admission to the hospital. There was a significant difference between both groups in plasma copeptin levels of the first dex/CRH test (cf. FIG. 1).

This group effect was not found in plasma copeptin levels of the second dex/CRH test (p=0.595; on average 60 days after admission), although there was still a strong effect on dex/CRH test outcome (e.g., ACTH AUC: p=0.005; cortisol AUC: p<0.001).

Next we tested for associations between plasma copeptin of the first and second dex/CRH test and ACTH and cortisol responses to the respective test. As can be seen in Table 2, we observe robust positive associations between integrative measures of the ACTH and cortisol response to both dex/CRH tests (AUC, Max) and copeptin levels. Also the net cortisol, and partly also the net ACTH responses particularly reflecting CRH effects show significant associations with copeptin.

TABLE 2

Associations between ACTH and cortisol responses to the first (on average six days after admission) and the second dex/CRH test (on average after 60 days) and respective plasma copeptin levels (N = 194 at the first dex/CRH test; N = 118 at the second dex/CRH test; results corrected for the effects of age and gender).

|  |  | Copeptin @ 1st DexCRH | Copeptin @ 2nd DexCRH |
|---|---|---|---|
| ACTH Baseline (after dex) | Correlation | .449 | .031 |
|  | p-value | .000 | .744 |
| ACTH Max (after CRH) | Correlation | .310 | .566 |
|  | p-value | .000 | .000 |
| ACTH AUC | Correlation | .231 | .519 |
|  | p-value | .001 | .000 |
| ACTH Net AUC (baseline corr.) | Correlation | .000 | .574 |
|  | p-value | .996 | .000 |
| Cortisol Baseline (after dex) | Correlation | .053 | .209 |
|  | p-value | .462 | .025 |
| Cortisol Max (after CRH) | Correlation | .151 | .436 |
|  | p-value | .037 | .000 |
| Cortisol AUC | Correlation | .185 | .438 |
|  | p-value | .010 | .000 |
| Cortisol Net AUC (baselin corr.) | Correlation | .233 | .451 |
|  | p-value | .001 | .000 |

Associations Between Copeptin and Depression Symptoms

To evaluate the effects of copeptin and HPA axis measures on concurrent depression symptoms, we evaluated the associations between these measures and the total score on the 21 item Hamilton Depression Rating Scale (HAND) obtained at the test day (or in close proximity to the test day). The results can be found in Table 3.

TABLE 3

Associations between ACTH, cortisol and copeptin responses to the first (on average six days after admission) and the second dex/CRH test (on average after 60 days) and depression symptoms evaluated with the HAMD scale (N = 194 at the first dex/CRH test; N = 118 at the second dex/CRH test; results corrected for the effects of age and gender).

|  |  | HAMD @ 1st DexCRH | HAMD @ 2nd DexCRH |
|---|---|---|---|
| ACTH Baseline (after dex) | Correlation | .169 | −.038 |
|  | p-value | .019 | .687 |
| ACTH Max (after CRH) | Correlation | .136 | −.104 |
|  | p-value | .061 | .266 |
| ACTH AUC | Correlation | .127 | −.108 |
|  | p-value | .079 | .250 |
| ACTH Net AUC (baseline corr.) | Correlation | .049 | −.109 |
|  | p-value | .504 | .244 |
| Cortisol Baseline (after dex) | Correlation | .261 | .031 |
|  | p-value | .000 | .740 |
| Cortisol Max (after CRH) | Correlation | .162 | −.064 |
|  | p-value | .025 | .497 |
| Cortisol AUC | Correlation | .197 | −.058 |
|  | p-value | .006 | .538 |

TABLE 3-continued

Associations between ACTH, cortisol and copeptin responses to the first (on average six days after admission) and the second dex/CRH test (on average after 60 days) and depression symptoms evaluated with the HAMD scale (N = 194 at the first dex/CRH test; N = 118 at the second dex/CRH test; results corrected for the effects of age and gender).

|  |  | HAMD @ 1st DexCRH | HAMD @ 2nd DexCRH |
|---|---|---|---|
| Cortisol Net AUC (baselin corr.) | Correlation | .071 | −.091 |
|  | p-value | .327 | .329 |
| Copeptin | Correlation | −.029 | −.121 |
|  | p-value | .687 | .197 |

Associations Between Change in Copeptin and Treatment Outcome

In the following analysis we evaluated the change in HPA axis parameters and copeptin between both dex/CRH tests as predictors for depression outcome. For this analysis, we included only patients with an HAMD score of at least 14 indicating moderate depression severity at the time of the first dex/CRH test. Furthermore, only patients with a second dex/CRH test within the first 8 weeks of hospitalisation were considered (average time of the second dex/CRH test: 31 days after admission). Outcome was evaluated as response after 8 weeks and as remission at the end of hospitalisation. All available data have been included. The results are presented in Table 4.

TABLE 4

Associations between change in ACTH, cortisol and copeptin responses to a second dex/CRH tests after to 8 weeks (on average after 31 days) and response after 8 weeks as well as remission at discharge as depression outcome (N = 209/159 for ACTH and cortisol, N = 52/51 for copeptin; results corrected for the effects of age and gender).

|  |  | Response @ 8 Weeks | Remission @ Discharge |
|---|---|---|---|
| ACTH Baseline (after dex) | OR | 1.05 | 1.06 |
|  | p-value | .112 | .161 |
| ACTH Max (after CRH) | OR | 1.01 | 1.02 |
|  | p-value | .224 | .227 |
| ACTH AUC | OR | 1.01 | 1.01 |
|  | p-value | .274 | .204 |
| ACTH Net AUC (baseline corr.) | OR | 1.01 | 1.01 |
|  | p-value | .856 | .849 |
| Cortisol Baseline (after dex) | OR | 1.02 | 1.01 |
|  | p-value | .064 | .275 |
| Cortisol Max (after CRH) | OR | 1.01 | 1.01 |
|  | p-value | .415 | .045 |
| Cortisol AUC | OR | 1.01 | 1.01 |
|  | p-value | .204 | .038 |
| Cortisol Net AUC (baseline corr.) | OR | 1.00 | 1.01 |
|  | p-value | .788 | .075 |
| Copeptin | OR | 1.00 | 1.00 |
|  | p-value | .965 | .975 |

Summary and Discussion

Dividing depressed inpatients in those with high vs. low HPA axis dysregulations at the time of admission to the hospital resulted in a clear effect on plasma copeptin, which was collected in the first of five blood samples collected during the dex/CRH test. This finding supports the role of elevated hypothalamic vasopressin levels as a key driver of HPA axis dysregulations in depression. In line with this finding, we observed medium to strong associations between parameters of the ACTH and cortisol response to the dex/CRH test and elevated plasma copeptin levels.

Example 2

Genetic polymorphisms that influence the extent of the ACTH response in the combined Dex/CRH test in patients with current moderate to severe depression were identified using genome-wide SNP analysis of epistasis with genetic variation in the AVPR1B gene, a key player in the pathways relating to the combined Dex/CRH test. These polymorphisms describe genetic variations that in interaction with genetic variation in the AVPR1B gene lead to major depression with CRH hyperdrive. Patients carrying the alleles/genotypes associated with a larger cortisol or ACTH response in the dex/CRH test should therefore profit from $V_{1B}$ antagonist treatment of depression and anxiety.

Patients:

Patients with unipolar or bipolar depression admitted as inpatients to the Max Planck Institute of Psychiatry (MPI), Munich, Germany, for treatment of a depressive episode were included in the study. Patients were diagnosed by psychiatrists according to the Diagnostic and Statistical Manual of Mental Disorders (DSM) IV criteria. Patients with bipolar disorder or depressive disorder due to a general medical or neurological condition were excluded, as were patients with a lifetime diagnosis of drug abuse and depressive symptoms secondary to alcohol or substance abuse or dependency. Ethnicity was recorded using a self-report sheet for nationality, first language and ethnicity of the patient and of all four grandparents.

All patients were Caucasian and part of the Munich-Antidepressant-Response-Signature (MARS) project (Hennings et al. Clinical characteristics and treatment outcome in a representative sample of depressed inpatients—findings from the Munich Antidepressant Response Signature (MARS) project. *J Psychiatr Res*. January 2009; 43(3):215-229; www.mars-depression.de). They were treated with antidepressant medications according to doctor's choice. Severity of depressive symptoms was assessed at admission and at the time of the dex-CRH test by trained raters using the 17-item Hamilton Depression Rating Scale (HAM-D) (Hamilton M. A rating scale for depression. *J Neurol Neurosurg Psychiatry*. 1960; 23:56-62). 352 patients fulfilling the criteria for at least a moderate to severe depressive episode (HAM-D≥18) at both time points and who had been administered a dex-CRH test within 10 days of in-patients admission and had genome-wide SNP data were included in this analysis. The study was approved by the Ethics Committee of the Ludwig Maximilians University in Munich, Germany, and written informed consent was obtained from all subjects.

Dex-CRH Test:

The dex-CRH test was administered as described in detail in Heuser et al. Shortly, subjects were pre-treated with 1.5 mg of dexamethasone per os at 11 pm. The following day, at 3 pm, 3.30 pm, 3.45 pm, 4 pm and 4.15 pm blood was drawn. An intravenous bolus of 100 μg of human CRH (Ferring, Kiel, Germany) was given at 3.02 pm. Plasma ACTH concentrations were assessed by an immunometric assay without extraction (Nichols Institute, San Juan Capistrano, Calif.; USA). The neuroendocrine response to the dex/CRH test was analyzed using the total area under the curve (AUC) of the ACTH response.

SNP Genotyping:

After enrollment in the study 40 ml of EDTA blood was drawn from each patient. DNA was extracted from fresh blood using the Puregene® whole blood DNA-extraction kit (Gentra Systems Inc; MN).

Genotyping was performed on Illumina Human 610 k quad genotyping arrays (Illumina Inc., San Diego, USA) according to the manufacturer's standard protocols. The average call rate exceeded 99%, with samples below 98% being either retyped or excluded from the study. The reproducibility for samples genotyped twice was 99.99% or better.

Figure 2:
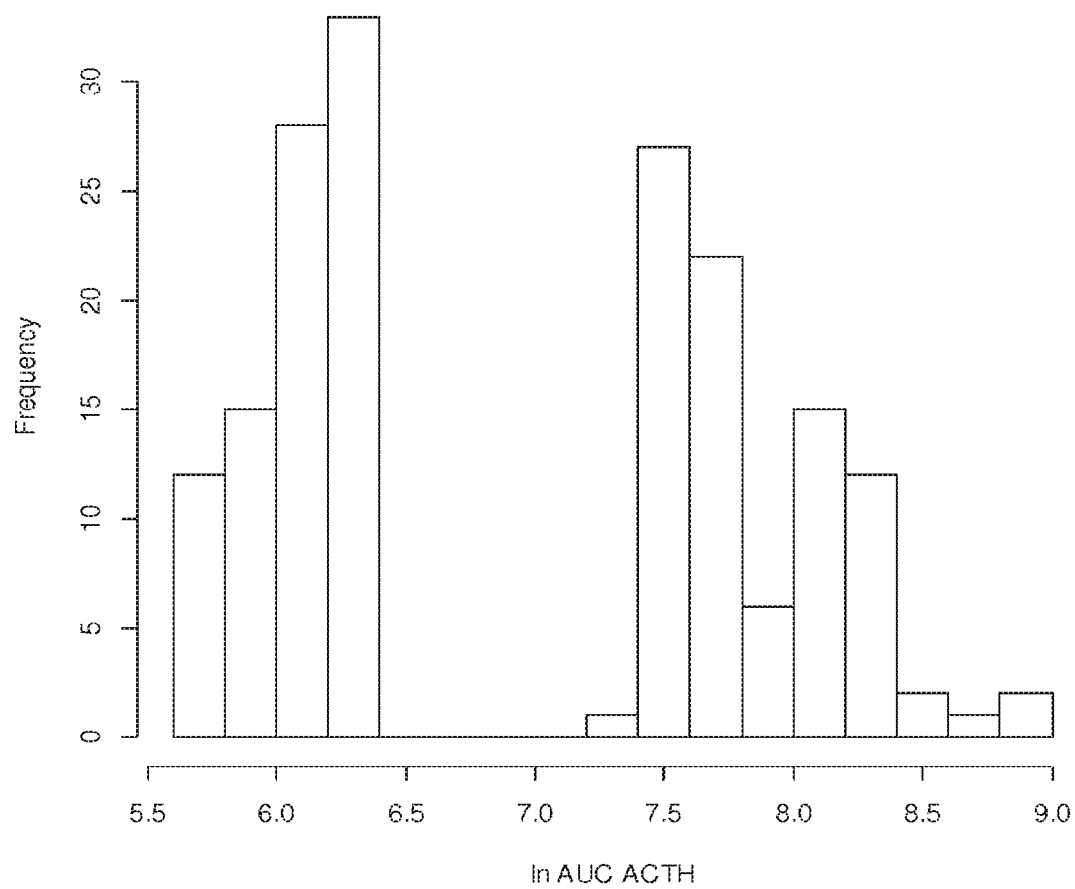
FIG. 2: Graph of the phenotypic distribution of ln(AAUC) at in-patient admission. The X-axis shows the ln of the AUC of the ACTH response and the Y-axis the frequency in total N/bin. #

Data Analysis:

To identify genetic predictors for the ACTH response to the dex/CRH test in patients with moderate to severe depression, the full sample of 352 patients was used. After natural log transformation of the AUC of the ACTH response in the dex-CRH test, an analysis of epistasis (gene by gene interaction with the AVPR1B SNP rs28373064) was used to determine SNPs associated with the quantitative phenotype natural log of the AUC of the ACTH response. This analysis was done genome wide and only SNPs with a P-value of $<1*10^{-5}$ were retained for the building of the genetic predictor. This resulted in a total of 14 SNPs. For the prediction analysis patients were dichotomized into high vs. low responders by selecting the top and the bottom quartile of the phenotype. This led to a number of 88 patients in each group. For the low responder group the natural log of the AUC of the ACTH ranged from 5.704 to 6.384, for the high responder group the range of the natural log of the AUC of the ACTH ranged from 7.399 to 8.980. See the corresponding histogram in FIG. 2 for the trait distribution in the two groups The 14 SNPs retained were then used predict either ACTH response status support vector machine" approach (implementation DTREG 10.6.21 www.dtreg.com). All values were derived from leave-one-out cross-validation.

Results:

The top 14 associations with ACTH response in interaction with AVPR1B genetic variation status are given in table 5. The genotypes for the 14 SNPs each were then used to predict high vs. low ACTH response status using interaction with AVPR1B genetic variation applying leave-one-out cross-validation.

The Results of the Prediction are Summarized Below:

For the prediction of the dichotomized high vs low ACTH response status in the dex-CRH test the following prediction values in the leave-one-out cross validation were achieved:

ACTH:
Accuracy=75.00%
True positive (TP)=69 (39.2%)
True negative (TN)=63 (35.8%)
False positive (FP)=25 (14.2%)
False negative (FN)=19 (10.8%)
Sensitivity=78.41%
Specificity=71.59%
Geometric mean of sensitivity and specificity=74.92%
Positive Predictive Value (PPV)=73.40%
Negative Predictive Value (NPV)=76.83%
Geometric mean of PPV and NPV=75.10%
Precision=73.40%
Recall=78.41%
F-Measure=0.7582
Area under ROC curve (AUC)=0.780475

Summary and Discussion

Using genome-wide SNP association data for the ACTH response in the dex/CRH test, a subset of 14 SNPs was identified that, in conjunction with the SNP rs28373064, can be used for an accurate, sensitive and specific prediction of these phenotypes in patients. Increased ACTH secretion in this test has been linked to a possible increase in central CRH/CRHR1 function. It is surprising that genetic polymorphisms, which act in interaction with genetic variation in the AVPR1B gene, without taking into consideration other factors such as endocrine measures, are suitable predictors of the ACTH response in the dex/CRH test.

These variants may be used to identify patients that may have CRH system hyperactivity when depressed. Patients with depression or anxiety disorders, classified into the high ACTH response group according to the genotypes of the presented 14 SNPs and the SNP rs28373064 will be more likely to respond to $V_{1B}$ antagonist treatment. This allows an enrichment of such patients for $V_{1B}$ antagonist treatment studies who should respond to this specific treatment.

TABLE 5

List of 14 SNPs used to predict high vs low ACTH response status allowing for interaction with genetic variation in the AVPR1B gene.

| SNP | Chromosome | Coordinate_HG18 | GeneVariant | P-value for association with ln AUC ACTH in epistasis with genetic variation in AVPR1B | GeneName |
| --- | --- | --- | --- | --- | --- |
| rs9880583 | chr3 | 20980315 | INTERGENIC | 6.31E−005 | N/A |
| rs13099050 | chr3 | 21028194 | INTERGENIC | 4.50E−005 | N/A |
| rs7441352 | chr4 | 55608691 | INTERGENIC | 1.68E−005 | N/A |
| rs730258 | chr4 | 68431265 | INTRONIC | 9.08E−005 | TMPRSS11D |
| rs12654236 | chr5 | 169540125 | INTERGENIC | 9.98E−005 | N/A |
| rs17091872 | chr8 | 19876257 | INTERGENIC | 9.77E−005 | N/A |
| rs12254219 | chr10 | 79113526 | INTERGENIC | 6.05E−005 | N/A |
| rs11575663 | chr10 | 115316093 | INTRONIC | 7.92E−005 | HABP2 |
| rs7080276 | chr10 | 123112960 | INTERGENIC | 8.87E−005 | N/A |
| rs7416 | chr11 | 10485077 | 3PRIME_UTR | 5.61E−005 | AMPD3 |
| rs12424513 | chr12 | 95088085 | INTERGENIC | 4.20E−005 | N/A |
| rs1035050 | chr17 | 44919011 | INTERGENIC | 9.77E−005 | N/A |
| rs9959162 | chr18 | 68100371 | INTERGENIC | 5.57E−005 | N/A |
| rs8088242 | chr18 | 68100758 | INTERGENIC | 6.06E−005 | N/A |

The invention claimed is:

1. Method for predicting a treatment response to a $V_{1B}$ receptor antagonist in a human patient with depressive symptoms and/or anxiety symptoms, wherein the copeptin concentration in a blood sample of said patient is determined, wherein an elevated copeptin concentration compared to copeptin concentration in individuals not suffering from anxiety and/or depressive symptoms and being at least 5 pmol/L is indicative for the patient responding to a treatment with a $V_{1B}$ receptor antagonist, wherein the patient is determined to have the elevated copeptin concentration and wherein a V1B receptor antagonist is administered to the patient.

2. Method according to claim 1, further comprising a step of pre-treating the patient with dexamethasone and subsequently determining the copeptin concentration in the blood sample.

3. Method according to claim 2, further comprising subjecting the patient to at least one combined dexamethasone/corticotropin test (dex/CRH test).

4. Method according to claim 1, wherein the elevated copeptin concentration indicative for a patient responding to a treatment with a vasopressin receptor antagonist is in the range of 5-7 pmol/L.

5. Method according to claim 2, wherein the elevated copeptin concentration indicative for a patient responding to a treatment with a vasopressin receptor antagonist is in the range of 5-7 pmol/L.

6. Method according to claim 3, wherein the elevated copeptin concentration indicative for a patient responding to a treatment with a vasopressin receptor antagonist is in the range of 5-7 pmol/L.

7. A method of treating a human patient with depressive symptoms and/or anxiety symptoms comprising predicting a treatment response to a V1B receptor antagonist in the human patient by determining the copeptin concentration in a blood sample of said patient, wherein an elevated copeptin concentration compared to copeptin concentration in individuals not suffering from anxiety and/or depressive symptoms and being at least 5 pmol/L is indicative for the patient responding to a treatment with a V1B receptor antagonist, and administering a V1B receptor antagonist to the patient if the elevated copeptin concentration has been determined in the blood sample, wherein the patient is determined to have the elevated copeptin concentration, and wherein a V1B receptor antagonist is administered to the patient.

* * * * *

SEQUENCE LISTING

<160> NUMBER OF SEQ ID NOS: 16

<210> SEQ ID NO 1
<211> LENGTH: 9
<212> TYPE: PRT
<213> ORGANISM: Homo sapiens

<400> SEQUENCE: 1

Cys Tyr Phe Gln Asn Cys Pro Arg Gly
1               5

<210> SEQ ID NO 2
<211> LENGTH: 52
<212> TYPE: DNA
<213> ORGANISM: Homo sapiens

<400> SEQUENCE: 2
tcctgcaccg gctagccggc tggcagaggg cgcgccaaca gccgccagcc ga            52

<210> SEQ ID NO 3
<211> LENGTH: 52
<212> TYPE: DNA
<213> ORGANISM: Homo sapiens

<400> SEQUENCE: 3
aaatgaagcc acttgtttct tctccaccta tgacctagac accccctccc ca            52

<210> SEQ ID NO 4
<211> LENGTH: 52
<212> TYPE: DNA
<213> ORGANISM: Homo sapiens

<400> SEQUENCE: 4
aatgaataag aagcctctca agacagaagg attcaacctt atagctttga ta            52

<210> SEQ ID NO 5
<211> LENGTH: 52
<212> TYPE: DNA
<213> ORGANISM: Homo sapiens

<400> SEQUENCE: 5
tcctctcccc ctatctctgc ttttcaacat tgtactggaa gtcctagcta at            52

<210> SEQ ID NO 6
<211> LENGTH: 52
<212> TYPE: DNA
<213> ORGANISM: Homo sapiens

<400> SEQUENCE: 6
agaaataaaa tcatttcata ttcatgcaat agatacaaga aatgtattaa ag            52

<210> SEQ ID NO 7
<211> LENGTH: 52
<212> TYPE: DNA
<213> ORGANISM: Homo sapiens

<400> SEQUENCE: 7
ggactgtttt tgtattcagt gcacagatgt gtgtgaagac acccagcatg tt            52

<210> SEQ ID NO 8
<211> LENGTH: 52
<212> TYPE: DNA
<213> ORGANISM: Homo sapiens

<400> SEQUENCE: 8
aatgcaaatt tttatcaagt acctacaatg tgcgggcaat tttgcaaggt gc    52

<210> SEQ ID NO 9
<211> LENGTH: 52
<212> TYPE: DNA
<213> ORGANISM: Homo sapiens

<400> SEQUENCE: 9
ctgtgtcctt gaagcccatg acagtgcctg acacaaagta gttgctcaat aa    52

<210> SEQ ID NO 10
<211> LENGTH: 52
<212> TYPE: DNA
<213> ORGANISM: Homo sapiens

<400> SEQUENCE: 10
ctttatttac aaaaacaaaa ctgctaagct tggcccaagg gcccttattt gc    52

<210> SEQ ID NO 11
<211> LENGTH: 52
<212> TYPE: DNA
<213> ORGANISM: Homo sapiens

<400> SEQUENCE: 11
gtccacgtga cttcacacat cagccaatga ggtctggcct ctgtcaccaa ac    52

<210> SEQ ID NO 12
<211> LENGTH: 52
<212> TYPE: DNA
<213> ORGANISM: Homo sapiens
<220> FEATURE:
<221> NAME/KEY: misc_feature
<222> LOCATION: (21)..(25)
<223> OTHER INFORMATION: n is a, c, g, or t

<400> SEQUENCE: 12
gtaaccggat gcattttttt nnnnnaaaat ttctcccta tctactatga tg    52

<210> SEQ ID NO 13
<211> LENGTH: 52
<212> TYPE: DNA
<213> ORGANISM: Homo sapiens

<400> SEQUENCE: 13
gcagccggac cctgtattga ggaggacggg cagggaaagc atgctttaga ga    52

<210> SEQ ID NO 14
<211> LENGTH: 52
<212> TYPE: DNA
<213> ORGANISM: Homo sapiens

<400> SEQUENCE: 14
ctccccatct ttgtattgat gtaagcctca cctctctgcc cactggcatc cg    52

<210> SEQ ID NO 15
<211> LENGTH: 52
<212> TYPE: DNA
<213> ORGANISM: Homo sapiens

<400> SEQUENCE: 15
tcctcctgat tgccttcaaa ttaggaaatc agttgaagtt cctgctttca ga    52

```
<210> SEQ ID NO 16
<211> LENGTH: 52
<212> TYPE: DNA
<213> ORGANISM: Homo sapiens

<400> SEQUENCE: 16
aacatctgac aaaaggtaag aactcaataa atgctttgat agaacttaaa ta            52
```